(12) United States Patent
Miller et al.

(10) Patent No.: US 11,766,203 B2
(45) Date of Patent: Sep. 26, 2023

(54) COAXIAL MICRONEEDLE ASSEMBLIES AND METHODS THEREOF

(71) Applicant: National Technology & Engineering Solutions of Sandia, LLC, Albuquerque, NM (US)

(72) Inventors: Philip Rocco Miller, Albuquerque, NM (US); Ronen Polsky, Albuquerque, NM (US); Nathaniel Bryant Pfeifer, Los Lunas, NM (US)

(73) Assignee: National Technology & Engineering Solutions of Sandia, LLC, Albuquerque, NM (US)

( * ) Notice: Subject to any disclaimer, the term of this patent is extended or adjusted under 35 U.S.C. 154(b) by 901 days.

(21) Appl. No.: 16/126,039

(22) Filed: Sep. 10, 2018

(65) Prior Publication Data

US 2019/0076075 A1    Mar. 14, 2019

Related U.S. Application Data

(60) Provisional application No. 62/558,194, filed on Sep. 13, 2017.

(51) Int. Cl.
*A61B 5/15* (2006.01)
*A61B 5/145* (2006.01)
(Continued)

(52) U.S. Cl.
CPC .... *A61B 5/150984* (2013.01); *A61B 5/14503* (2013.01); *A61B 5/14532* (2013.01); *A61B 5/14539* (2013.01); *A61B 5/14865* (2013.01); *A61B 5/150022* (2013.01); *A61B 5/150396* (2013.01); *A61B 5/150282* (2013.01);
(Continued)

(58) Field of Classification Search
CPC ......... A61B 5/150984; A61B 5/14503; A61B 5/14532; A61B 5/14539; A61B 5/14865; A61B 5/150022; A61B 5/150396; A61B 5/150282; A61B 2562/028;
(Continued)

(56) References Cited

U.S. PATENT DOCUMENTS 6,443,179 B1    9/2002    Benavides et al.
6,464,849 B1 *  10/2002   Say ................... C12Q 1/004
                                                204/403.01
(Continued)

FOREIGN PATENT DOCUMENTS

WO    WO2010022252 A2    2/2010
WO    WO2013058879 A2    4/2013

OTHER PUBLICATIONS

Windmiller, J.R. et al., "Microneedle Array-Based Carbon Paste Amperometric Sensors and Biosensors", Analyst, 2011, pp. 1846-1851, vol. 136.
(Continued)

*Primary Examiner* — Jason M Sims
*Assistant Examiner* — Mitchell E Alter
(74) *Attorney, Agent, or Firm* — Kevin W. Bieg; Helen S. Baca

(57) ABSTRACT

The present invention is directed to devices including one or more hollow needles and a transducing wire disposed within at least one needle. In particular instances, arrays of such needles can be employed. Methods for fabricating and using such devices are also disclosed herein.

9 Claims, 8 Drawing Sheets

(51) Int. Cl.
*A61B 5/1486* (2006.01)
*A61M 37/00* (2006.01)

(52) U.S. Cl.
CPC .... *A61B 2562/028* (2013.01); *A61M 37/0015* (2013.01); *A61M 2037/003* (2013.01); *A61M 2037/0053* (2013.01); *A61M 2037/0061* (2013.01)

(58) Field of Classification Search
CPC ........ A61M 37/0015; A61M 2037/003; A61M 2037/0053; A61M 2037/0061
USPC ......................................................... 600/345
See application file for complete search history.

(56) References Cited

U.S. PATENT DOCUMENTS

| | | | |
|---|---|---|---|
| 6,548,895 | B1 | 4/2003 | Benavides et al. |
| 6,908,453 | B2 | 6/2005 | Fleming et al. |
| 7,344,499 | B1 | 3/2008 | Prausnitz et al. |
| 9,987,427 | B1* | 6/2018 | Polsky .................. A61B 5/155 |
| 2011/0224515 | A1 | 9/2011 | Mir et al. |
| 2013/0225957 | A1* | 8/2013 | Kawamoto ........ A61B 5/14865 600/347 |
| 2014/0336487 | A1* | 11/2014 | Wang .................. A61B 5/1473 600/352 |
| 2015/0313521 | A1* | 11/2015 | Say .................. A61B 5/150396 600/347 |
| 2016/0296149 | A1* | 10/2016 | Polsky .............. A61B 5/14546 |
| 2018/0338713 | A1* | 11/2018 | Polsky .................. A61B 5/685 |

OTHER PUBLICATIONS

Justino, C.I.L. et al., "Review of Analytical Figures of Merit of Sensors and Biosensors in Clinical Applications", Trends in Analytical Chemistry 2010, pp. 1172-1183, vol. 29.

Gittard, S.D. et al., "Two Photon Polymerization of Microneedles for Transdermal Drug Delivery", Expert Opin. Drug Deliv., 2010, pp. 513-533, vol. 7.

Miller, P.R. et al., "Multiplexed Microneedle-Based Biosensor Array for Characterization of Metabolic Acidosis", Talanta, 2012, pp. 739-742, vol. 88.

Kim, D-H, et al. "Epidermal Electronics", Science, 2011, pp. 838-846, vol. 333.

Gubala, V. et al., "Point of Care Diagnostics: Status and Future", Analytical Chemistry 2012, pp. 487-515, vol. 84.

Windmiller, J.R. et al., "Wearable Electrochemical Sensors and Biosensors: A Review", Electroanalysis, 2013, pp. 29-46, vol. 25.

Jia, W. et al. "Electrochemical Tattoo Biosensors for Real-Time Noninvasive Lactate Monitoring in Human Perspiration", Analytical Chemistry, 2013, pp. 6553-6560, vol. 85.

* cited by examiner

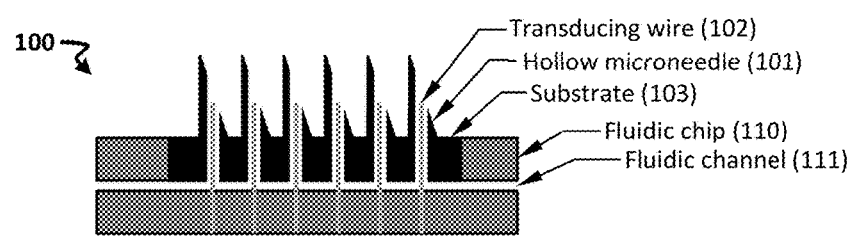
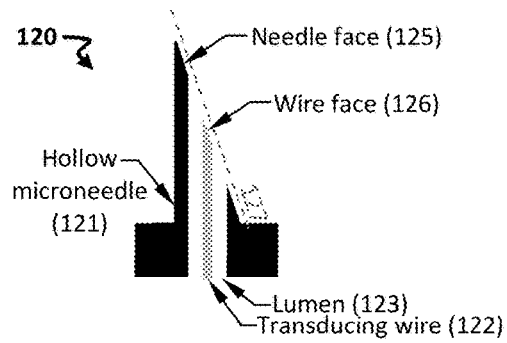
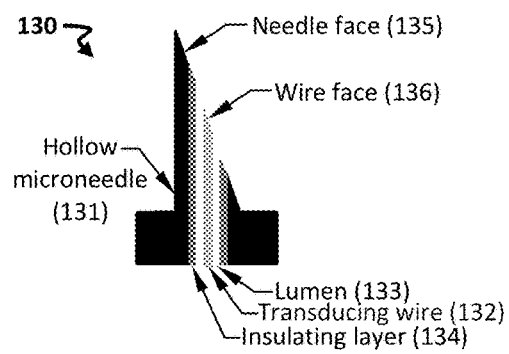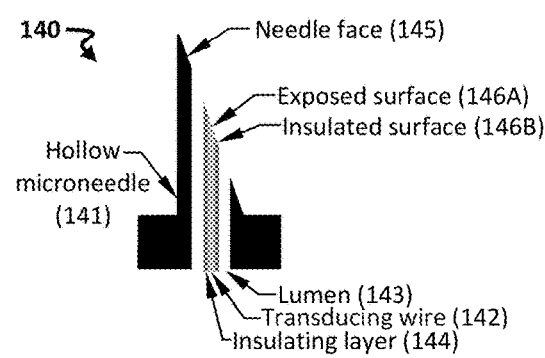
FIG. 1A
FIG. 1B
FIG. 1C
FIG. 1D

COAXIAL MICRONEEDLE ASSEMBLIES AND METHODS THEREOF

CROSS-REFERENCE TO RELATED APPLICATION

This application claims the benefit of U.S. Provisional Application No. 62/558,194, filed Sep. 13, 2017, which is incorporated herein by reference.

STATEMENT OF GOVERNMENT INTEREST

This invention was made with Government support under Contract No. DE-NA0003525 awarded by the United States Department of Energy/National Nuclear Security Administration. The Government has certain rights in the invention.

FIELD OF THE INVENTION

The present invention is directed to devices including one or more hollow needles and a transducing wire disposed within at least one needle. In particular instances, arrays of such needles can be employed. Methods for fabricating and using such devices are also disclosed herein.

BACKGROUND OF THE INVENTION

Health monitoring continues to benefit from advancing technologies related to miniaturized sensors, wearable devices, and wireless networking. Non-invasive modalities do provide beneficial health data, e.g., optical absorption correlated with blood perfusion or heart rate. Yet other relevant biomarkers require access to a patient's fluid sample, e.g., glucose measurement using a blood sample, such as by invasive sampling with a needle through the skin.

Minimally invasive monitoring continues to be an attractive alternative to invasive sampling and monitoring. In one non-limiting instance, microneedles can be employed to minimize skin penetration and nerve contact, while providing access to relevant biofluid samples. Interfacing microneedles with sensing components can provide a miniaturized, multiplex platform for detecting various types of biomarkers. Thus, there is a need for improved devices to implement such platforms.

SUMMARY OF THE INVENTION

The present invention relates, in part, to a device including at least one hollow needle and at least one transducing wire disposed within the hollow needle. If both the needle and the wire are composed of electrically conductive materials, then electrical isolation may be desired. Thus, in some embodiments, an insulating layer is disposed upon a surface of the hollow needle (e.g., upon an interior surface facing the hollow lumen) and/or upon a surface of the transducing wire.

In a first non-limiting aspect, the present invention features a device including: a hollow needle; at least one transducing wire disposed within a lumen of the needle; and an insulating layer disposed within at least a portion of a surface of the lumen and/or upon at least a portion of a surface of the transducing wire.

In some embodiments, a distal end of the hollow needle includes a puncturing edge (e.g., a tapered point, a sharpened bevel, or one or more prongs). In particular embodiments, the puncturing edge of the needle includes a needle face, and the transducing wire includes a wire face disposed at a distal end. In other embodiments, a plane of the needle face and a plane of the wire face are sufficiently parallel (e.g., the two planes do not intersect over the distance of the width, length, or diameter of the needle).

In some embodiments, the insulating layer is disposed upon the surface (e.g., or a portion thereof) of the transducing wire. In other embodiments, the insulating layer is disposed within the surface (e.g., or a portion thereof) of the lumen.

In some embodiments, the device further includes a conductive component providing an electrical connection to the transducing wire. In other embodiments, the conductive component is electrically connected to a distal end of the transducing wire. In yet other embodiments, the proximal end of the transducing wire is electrically connected to a sensing element (e.g., a potentiostat). Exemplary conductive components are described herein (e.g., a carbon-based paste or a conductive polymer).

In some embodiments, a distal end of the transducing wire includes an exposed surface. In particular embodiments, the exposed surface is conductive and optionally includes one or more electrochemical modifications. In other embodiments, a conductive component is disposed on the exposed surface of the transducing wire. In yet other embodiments, the conductive component includes one or more entrapped capture agents (e.g., any capture agent described herein, such as an enzyme, a protein, an antibody, etc.).

In a second non-limiting aspect, the present invention features a device including: a plurality of hollow needles, where each needle has an interior surface facing a hollow lumen; a plurality of transducing wires, where at least one transducing wire is disposed within the lumen of each needle; and an insulating layer disposed within a surface of the lumen and/or upon a surface of the transducing wire. In some embodiments, the device further includes: a substrate coupled to the plurality of hollow needles, where the substrate includes one or more inlets in fluidic communication with a proximal end of at least one needle; and a first channel coupled to the substrate and in fluidic communication with at least one inlet of the substrate.

In some embodiments, the device further includes a sensing component, a delivery component, and/or an electronic component. In particular embodiments, the sensing component can include one or more sensing transducers (e.g., in fluidic communication with the first channel). In other embodiments, at least one sensing transducer is configured to detect one or more markers in a sample. In some embodiments, the delivery component includes one or more depots configured to contain one or more therapeutic agents, capture agents, and/or labels (e.g., any described herein). In other embodiments, the electronic component includes circuitry configured for signal processing, signal control, power control, and/or communication signaling. In particular embodiments, the electronic component is connected electrically to the sensing component and/or the delivery component.

In a third non-limiting aspect, the present invention features a biosensor device including: a working electrode, a reference electrode, and an auxiliary electrode. In some embodiments, the working electrode includes a first hollow needle having a hollow lumen; a first transducing wire disposed within the lumen; and a conductive component disposed on the exposed surface of the first transducing wire (e.g., where the conductive component includes one or more entrapped capture agents, such as any described herein). In some embodiments, the reference electrode includes a second hollow needle having a hollow lumen; and a second transducing wire disposed within the lumen. In some embodiments, the auxiliary electrode includes a third hollow needle having a hollow lumen.

In some embodiments, the device (e.g., the biosensor device) includes an insulating layer disposed within a surface (e.g., or a portion thereof) of at least one of the hollow lumens and/or upon a surface of at least one of the first or second transducing wires.

In some embodiments, the device (e.g., the biosensor device) includes a substrate coupled to the working electrode, the reference electrode, and the auxiliary electrode, where the substrate includes one or more inlets in fluidic communication with a proximal end of at least one needle. In other embodiments, the device further includes a first channel coupled to the substrate and in fluidic communication with at least one inlet of the substrate.

In some embodiments, the device (e.g., a biosensor device) further includes a control electrode. In some embodiments, the control electrode includes a fourth hollow needle having a hollow lumen; a fourth transducing wire disposed within the lumen of the needle; and a conductive component disposed on the exposed surface of the transducing wire. In particular embodiments, the conductive component does not include one or more entrapped capture agents.

In some embodiments, a transducing wire (e.g., the first, second, third, and/or fourth transducing wire) has an exposed surface at a distal end. In particular embodiments, the exposed surface is electrically conductive.

In some embodiments, the entrapped capture agent includes an entrapped enzyme.

In a fourth non-limiting aspect, the present invention features a method of fabricating a device, the method including: providing a first transducing wire including an external surface; coating at least a portion of the external surface with an insulating layer, thereby providing a first insulated wire; inserting the first insulated wire within a hollow lumen of a hollow needle, thereby providing a first inserted wire; trimming the first inserted wire to provide an exposed surface disposed at a distal end of the first transducing wire; and depositing a conductive component upon the exposed surface of the transducing wire. In particular embodiments, the conductive component includes one or more entrapped capture agents.

In a fifth non-limiting aspect, the present invention features a method of fabricating a device, the method including: providing a first hollow needle including an interior surface facing a hollow lumen; coating at least a portion of the interior surface of the lumen with an insulating layer, thereby providing a first insulated needle; inserting a first transducing wire within a hollow lumen of a hollow needle, thereby providing a first inserted wire; trimming the first inserted wire to provide an exposed surface disposed at a distal end of the first transducing wire; and depositing a conductive component upon the exposed surface of the transducing wire (e.g., where the conductive component optionally includes one or more entrapped capture agents).

In some embodiments (e.g., of any method herein), the method further includes (e.g., after the inserting step, the trimming step, and/or the depositing step): providing a second transducing wire within the hollow lumen of the hollow needle, thereby providing a multiplexed needle, where the second transducing wire optionally includes an insulating layer.

In another aspect, the present invention features a disposable cartridge (e.g., a disposable cartridge module). In some embodiments, the disposable cartridge includes a barrel including an internal volume, a distal end, and a proximal end, where the distal end of the barrel is coupled (e.g., directly coupled or indirectly coupled, such as by way of a cap structure) to a plurality of hollow needles, a plurality of transducing wires, and a substrate (e.g., any hollow needle (s) and transducing wire(s) and substrate herein) and the proximal end of the barrel includes an opening; and a locking member disposed on a surface portion defining the internal volume. In other embodiments, the module further includes a sealing member disposed on a surface portion defining the internal volume.

In another aspect, the present invention features a detector (e.g., a detector module). In some embodiments, the first channel and the one or more transducers (e.g., any described herein) are configured as a detector module. In other embodiments, the detector includes a body (e.g., configured to contain the one or more transducers and the first channel), where the body includes a distal section and a proximal section; a central bore disposed within the body (e.g., and in fluidic communication with the first channel); and a mounting shaft disposed on the distal section of the body, where the mounting shaft is configured to be inserted into the opening of the disposable cartridge (e.g., any herein, including module forms thereof). In further embodiments, the detector includes a fitting structure disposed on an outer surface portion of the mounting shaft, where the fitting structure is configured to interface with the locking member of the disposable cartridge module; and/or a sealing structure disposed on an outer surface portion of the mounting shaft, where the sealing structure is configured to interface with the sealing member of the disposable cartridge module In yet another aspect, the present invention features a platform including a disposable cartridge module (e.g., any described herein) and a handheld module (e.g., any described herein, such as that described for a detector that is configured for handheld use). In some embodiments, the handheld module includes a body including a distal section and a proximal section; a central bore disposed within the body and in fluidic communication with the disposable cartridge module; and a mounting shaft disposed on the distal section of the body, where the mounting shaft is configured to be inserted into the opening of the disposable cartridge module. In some embodiments, the handheld module further includes a fitting structure disposed on an outer surface portion of the mounting shaft, where the fitting structure is configured to interface with the locking member of the disposable cartridge module; and/or a sealing structure disposed on an outer surface portion of the mounting shaft, where the sealing structure is configured to interface with the sealing member of the disposable cartridge module.

In other embodiments, the body further includes a handle disposed on the proximal section. In some embodiments, the body includes one or more sensing transducers (e.g., any described herein, such as one or more of an electrode and/or an ion selective electrode, including a reference electrode and/or a counter electrode) in fluidic communication with the internal volume. In other embodiments, at least one sensing transducer is configured to detect one or more markers in the sample. In other embodiments, the body further includes a pumping mechanism (e.g., a passive channel, an active pump, a vacuum source, etc.) configured to transport the sample from the hollow needles and/or the internal volume into the central bore.

In any embodiment herein, the needle has an interior surface facing a hollow lumen and an exterior surface, and a distal end of the exterior surface includes a puncturing edge.

In any embodiment herein, the needle has a length of more than about 0.5 mm and/or a width or diameter of less than about 1 mm. In some embodiments, at least one needle has a length of more than about 0.5 mm or from about 0.1 mm to about 7 mm (e.g., from 0.1 mm to 0.5 mm, 0.1 mm to 1 mm, 0.1 mm to 1.5 mm, 0.1 mm to 2 mm, 0.1 mm to 2.5 mm, 0.1 mm to 3 mm, 0.1 mm to 3.5 mm, 0.1 mm to 4 mm, 0.1 mm to 4.5 mm, 0.1 mm to 5 mm, 0.2 mm to 0.5 mm, 0.2 mm to 1 mm, 0.2 mm to 1.5 mm, 0.2 mm to 2 mm, 0.2 mm to 2.5 mm, 0.2 mm to 3 mm, 0.2 mm to 3.5 mm, 0.2 mm to 4 mm, 0.2 mm to 4.5 mm, 0.2 mm to 5 mm, 0.2 mm to 7 mm, 0.3 mm to 0.5 mm, 0.3 mm to 1 mm, 0.3 mm to 1.5 mm, 0.3 mm to 2 mm, 0.3 mm to 2.5 mm, 0.3 mm to 3 mm, 0.3 mm to 3.5 mm, 0.3 mm to 4 mm, 0.3 mm to 4.5 mm, 0.3 mm to 5 mm, 0.3 mm to 7 mm, 0.5 mm to 1 mm, 0.5 mm to 1.5 mm, 0.5 mm to 2 mm, 0.5 mm to 2.5 mm, 0.5 mm to 3 mm, 0.5 mm to 3.5 mm, 0.5 mm to 4 mm, 0.5 mm to 4.5 mm, 0.5 mm to 5 mm, 0.5 mm to 7 mm, 0.7 mm to 1 mm, 0.7 mm to 1.5 mm, 0.7 mm to 2 mm, 0.7 mm to 2.5 mm, 0.7 mm to 3 mm, 0.7 mm to 3.5 mm, 0.7 mm to 4 mm, 0.7 mm to 4.5 mm, 0.7 mm to 5 mm, 0.7 mm to 7 mm, 1 mm to 1.5 mm, 1 mm to 2 mm, 1 mm to 2.5 mm, 1 mm to 3 mm, 1 mm to 3.5 mm, 1 mm to 4 mm, 1 mm to 4.5 mm, 1 mm to 5 mm, 1 mm to 7 mm, 1.5 mm to 2 mm, 1.5 mm to 2.5 mm, 1.5 mm to 3 mm, 1.5 mm to 3.5 mm, 1.5 mm to 4 mm, 1.5 mm to 4.5 mm, 1.5 mm to 5 mm, 1.5 mm to 7 mm, 3 mm to 3.5 mm, 3 mm to 4 mm, 3 mm to 4.5 mm, 3 mm to 5 mm, and 3 mm to 7 mm). In other embodiments, the plurality of microneedles is provided in an array (e.g., two, three, four, five, six, seven, eight, nine, ten, fifteen, twenty, or more needles in array). In other embodiments, at least one hollow needle includes a polymer, a metal, silicon, glass, a composite material, or a combination thereof.

In any embodiment herein, at least one of the hollow needles is a hollow microneedle. In another embodiment, each and every hollow needle is a hollow microneedle.

In any embodiment herein, an array of needles can be provided or configured as a disposable cartridge module (e.g., any disposable cartridge described herein). In further examples, the first channel and/or one or more transducers can be provided or configured as a detector module (e.g., any detector herein).

In any embodiment herein, the transducing wire has an exposed surface at a distal end. In particular embodiments, the exposed surface is electrically conductive. In other embodiments, the exposed surface includes a conductive component providing an electrical connection to the transducing wire.

In any embodiment herein, the fluidic channel includes an array of channels configured for fluidic communication between an array of needles and a sensing component. In other embodiments, the array of channels is configured for fluidic communication between an array of needles and an array of sensing components (e.g., an electrode (e.g., a planar electrode, a three-dimensional electrode, a porous electrode, a disk electrode, a spherical electrode, a plate electrode, a hemispherical electrode, a microelectrode, and a nanoelectrode, or an array thereof), an ion selective electrode (e.g., including a porous material and one or more ionophores), an optical sensor, an array of any of these, and combinations thereof).

In any of the embodiments herein, at least one needle, transducing wire, substrate, fluidic channel, and/or sensing transducer further includes a modified surface (e.g., surface-modified with one or more capture agents, such as one or more antibodies for detecting one or more markers, enzymes, etc., as well as any described herein). In other embodiments, the modified surface includes a conductive material (e.g., a conductive polymer, such as poly(bithiophene), polyaniline, or poly(pyrrole), such as dodecylbenzenesulfonate-doped polypyrrole; a metal, such as metal nanoparticles, metal microparticles, or a metal film; or a nanotube). In yet other embodiments, the modified surface includes a linking agent (e.g., a diazonium compound, as described herein). In further embodiments, the modified surface includes a label (e.g., optionally attached to a surface by a linking agent).

In any of the embodiments herein, at least one needle (e.g., disposed within the lumen, on the interior surface, and/or on the exterior surface), transducing wire (e.g., disposed on the surface), substrate, fluidic channel (e.g., disposed within the channel), chamber, and/or sensing transducer (e.g., disposed on one or more electrodes, dielectrics, etc.) further includes a substance (e.g., one or more capture agents, electroactive components, linking agents, or any substance described herein).

In any of the embodiments herein, the needles, transducing wires, first channel, and/or transducers are, independently, provided in a high-density array. In further embodiments, the high-density array includes a modified surface (e.g., further including a linking agent, such as any described herein, including a diazonium compound).

In any of the embodiments herein, the device includes one or more components (e.g., the plurality of hollow needles, the plurality of transducing wires, the substrate, the first channel, and the one or more transducers) integrated into a single structure (e.g., a monolithic structure, where each of the components are bonded together to form a single structure). In further embodiments, each of the components (e.g., the plurality of hollow needles, the plurality of transducing wires, the substrate including the needles, the first channel, and the one or more transducers) is embedded in the same substrate. In further embodiments, each of the components (e.g., the plurality of hollow needles, the substrate including the needles, the transducing wires, the first channel, and the one or more transducers) is embedded in different substrates (e.g., where the different substrates are bonded to form a multilayer device).

In any of the embodiments herein, the device includes one or more components (e.g., the plurality of hollow needles, the plurality of transducing wires, the substrate, the first channel, and the one or more transducers) configured into separate modules (e.g., reusable or disposable modules).

In any of the embodiments herein, the device includes multiples substrates (e.g., configured in multiple layers).

In any of the embodiments herein, the device is configured in a package (e.g., a packaged chip having a housing for the device of the invention). In yet other embodiments, the device includes a sample processing module (e.g., including one or more sample chambers, valves, etc.,) in fluidic communication with a cartridge module and a detection module (e.g., a handheld module).

In any embodiment herein, the device includes one or more components to operate the transducing wire (e.g., a power source, a data-processing circuit powered by the power source and electrically connected to the transducer (e.g., a counter electrode, a reference electrode, and at least one said working electrode) and/or a data output port for the data-processing circuit).

In any of the embodiments herein, the device further includes one or more components for relaying the presence or absence of one or more markers in the sample. Exemplary components include a data output port for the data-processing circuit, an analog-to-digital converter, a radiofrequency module, a cable, and/or a telemetry unit (e.g., configured to receive processed data from a data-processing circuit electrically connected to the transducer and to transmit the data wirelessly).

In any embodiment herein, the device includes one or more mixing chambers, reaction chambers, reagents chambers, lysing chambers, washing chamber, elution chambers, extraction chambers, and/or collection chambers, where each of the chambers, if present, is in fluidic communication with the first channel. In other embodiments, the device includes at least one chamber in fluidic communication with another chamber (e.g., one or more reaction chambers in fluidic communication with at least one mixing chamber; one or more reagent chambers in fluidic communication with at least one mixing chamber and/or reaction chamber; one or more washing chambers in fluidic communication with at least one mixing chamber, reagent chamber, and/or reaction chamber).

In any embodiment herein, the device includes one or more additional components. Exemplary components include a pump (e.g., configured to facilitate the flow of the sample (e.g., sampled biological fluid) from at least one needle toward a channel, a sensing component, etc.); a power source; a data-processing circuit (e.g., powered by the power source and electrically connected to a sensing component, such as a counter electrode, a reference electrode, and/or a working electrode); a telemetry unit (e.g., configured to receive processed data from the data-processing circuit and to transmit the data wirelessly).

In any of the embodiments herein, the device includes one or more of a filter, a permeable or semi-permeable membrane, a valve, a chamber (e.g., any described herein, including reservoirs), a pump, a probe, a multifunctional sensor, a feedback resistor, a microscale light-emitting diode, an active/passive circuit element, an actuator, a wireless power coil, a device for radio frequency (RF) communications, a temperature sensor, a photodetector, a photovoltaic cell, a diode, and/or a liner with an adhesive layer (e.g., for affixing the device to a user).

Definitions

As used herein, the term "about" means +/−10% of any recited value. As used herein, this term modifies any recited value, range of values, or endpoints of one or more ranges.

By "fluidic communication," as used herein, refers to any duct, channel, tube, pipe, chamber, or pathway through which a substance, such as a liquid, gas, or solid may pass substantially unrestricted when the pathway is open. When the pathway is closed, the substance is substantially restricted from passing through. Typically, limited diffusion of a substance through the material of a plate, base, and/or a substrate, which may or may not occur depending on the compositions of the substance and materials, does not constitute fluidic communication.

As used herein, "linked" or "linking" is understood to mean attached or bound by covalent bonds, non-covalent bonds, and/or linked via van der Waals forces, hydrogen bonds, and/or other intermolecular forces.

By "microfluidic" or "micro" is meant having at least one dimension that is less than 1 mm. For instance, a microfluidic structure (e.g., any structure described herein) can have a length, width, height, cross-sectional dimension, circumference, radius (e.g., external or internal radius), or diameter that is less than 1 mm.

By "sample" is meant any specimen obtained from a subject, a plant, an environment, a chemical material, a biological material, or a manufactured product. The sample can include any useful material, such as biological (e.g., genomic) and/or chemical matter.

By "subject" is meant a human or non-human animal (e.g., a mammal). Exemplary non-human animals include livestock (e.g., cattle, goat, sheep, pig, poultry, farm fish, etc.), domestic animals (e.g., dog, cat, etc.), or captive wild animals (e.g., a zoo animal).

As used herein, the terms "top," "bottom," "upper," "lower," "above," and "below" are used to provide a relative relationship between structures. The use of these terms does not indicate or require that a particular structure must be located at a particular location in the apparatus.

Other features and advantages of the invention will be apparent from the following description and the claims.

BRIEF DESCRIPTION OF THE DRAWINGS

FIG. 1A-1D shows schematics of an exemplary device including a hollow needle and a transducing wire. Provided are cross-sectionals views an exemplary device 100 having an array of hollow microneedles 101 and an array of transducing wires 102 (FIG. 1A), an exemplary assembly 120 including a hollow microneedle 121 and a transducing wire 122 disposed within the lumen 123 of the microneedle (FIG. 1B), another exemplary assembly 130 including a hollow microneedle 131, a transducing wire 132, and an insulating layer 134 disposed on a surface of the lumen 133 of the microneedle (FIG. 1C), and yet another exemplary assembly 140 including a hollow microneedle 141, a transducing wire 142, and an insulating layer 144 disposed on a surface of the wire (FIG. 1D).

DETAILED DESCRIPTION OF THE INVENTION

Figure 2:
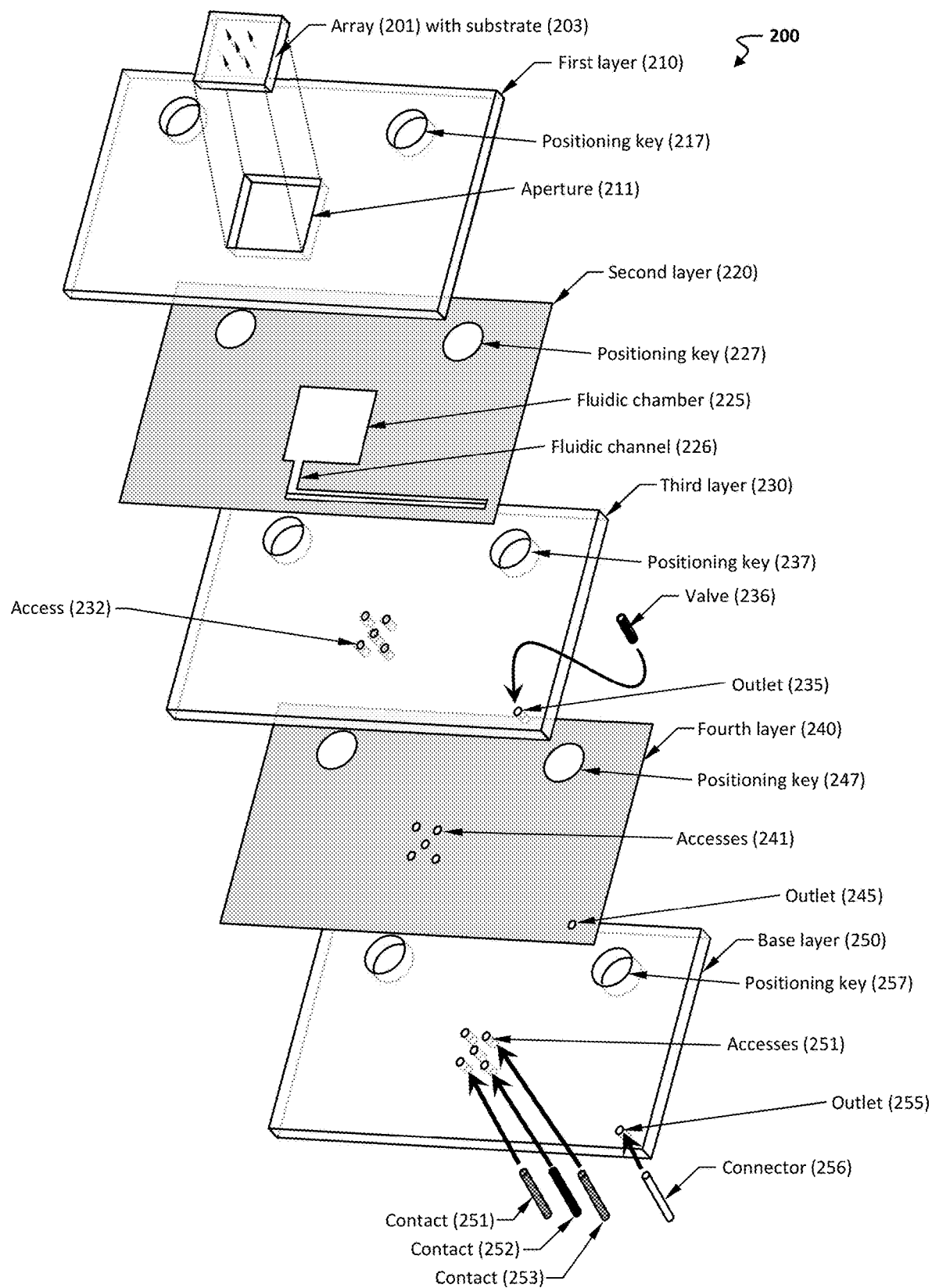
FIG. 2 shows an exploded view of another exemplary manifold 200.

The present invention relates to use of a hollow needle (e.g., a hollow microneedle) in conjunction with a transducing wire disposed within the lumen of the needle. In this manner, the coaxial assembly can be employed within a device for any useful purpose, e.g., to obtain one or more electrochemical measurements in a minimally invasive manner when the assembly is placed in proximity to a subject's skin. In one non-limiting instance, a minimally invasive electrochemical sensing and biosensing system can be created within a single hollow microneedle, which reduces cost, size, and materials required for an on-body measurement.

FIG. 1A provides an exemplary device 100 including an array of hollow microneedles 101 and an array of transducing wires 102, in which a single wire is disposed within each lumen of the microneedle. Each needle can be characterized by a distal end (e.g., having a puncturing edge) and a proximal end (e.g., in proximity to the substrate). The needle can, in some instances, provide a protective structure during insertion and can be used as a reference material in its native state or by coating with another metal more commonly used in electrochemistry (e.g., a noble metal, such as silver, gold, or platinum).

The needle-and-wire assembly can include a substrate 103 coupled to the needles. The substrate 103 can include one or more inlets in fluidic communication with a proximal end of the needle. The assembly can be interfaced with a fluidic chip 110, which can include a fluidic channel 111 in fluidic communication with at least one inlet of the substrate 103.

The needle and transducing wire can be oriented in any useful manner. In one instance, a face disposed at the distal end of the transducing wire is oriented to be sufficiently parallel to a face of the puncturing edge of the hollow needle. In this manner, upon insertion of the needle into the subject, the distal end of the transducing wire will not sustain significant damage.

FIG. 1B provides an exemplary schematic of an assembly 120 including a hollow microneedle 121 and a transducing wire 122 disposed within the lumen 123 of the needle. As can be seen, the distal end of the needle includes a needle face 125, and the distal end of the transducing wire includes a wire face 126. These faces can be characterized by a plane that extends along the face. As can be seen, the plane of the needle face 125 and the plane of the wire face 126 are sufficiently parallel along a non-intersecting plane 127. In this way, the plane of the faces of the needle and wire can be oriented in any beneficial manner.

The needle and transducing wire may be formed from any useful material. If both the needle and the wire are composed of conductive materials, then electrical isolation may be beneficial. Thus, the needle and/or the transducing wire may be insulated (e.g., with an insulating layer disposed on a surface) in any useful manner. In some instances, forming an insulating layer upon the transducing wire may provide additional structural stability to an otherwise thin wire. In some non-limiting instance, the transducing wire has a diameter or width of from about 5 µm to 300 µm (e.g., from about 10 µm to about 50 µm, or a dimension, such as a diameter, that is less than a dimension, such as a diameter, of the lumen of the microneedle).

FIG. 1C provides a schematic of an exemplary assembly 130 including a hollow microneedle 131 and a transducing wire 132 disposed within the lumen 133 of the needle. As can be seen, the needle face 135 and the wire face 136 are sufficiently parallel to each other. In addition, an insulating layer 134 is disposed within a surface of the lumen. In this manner, electric isolation is achieved between the transducing wire and the microneedle. If a second transducing wire is desired within the lumen, then a further insulating layer may be desired upon a surface of that second transducing wire.

FIG. 1D provides another schematic of an exemplary assembly 140 including a hollow microneedle 141 and a transducing wire 142 disposed within the lumen 143 of the needle. Here, the insulation layer 144 is disposed upon a surface of the transducing wire. The needle face 145 and the wire face are fairly parallel, and the wire face is further characterized by an exposed surface 146A and an insulated surface 146B. The exposed surface 146A can be modified to provide conductive component. In use, when the exposed surface of the transducing wire is placed within a subject's sample, then the conductive component interacts with an electrically active target. This interaction produces an electrochemical signal that is conducted through the transducing wire, which in turn is electrically connected to a sensing component (e.g., a potentiostat) capable of providing detection signal that indicates the presence or absence of the target.

Figure 12A:
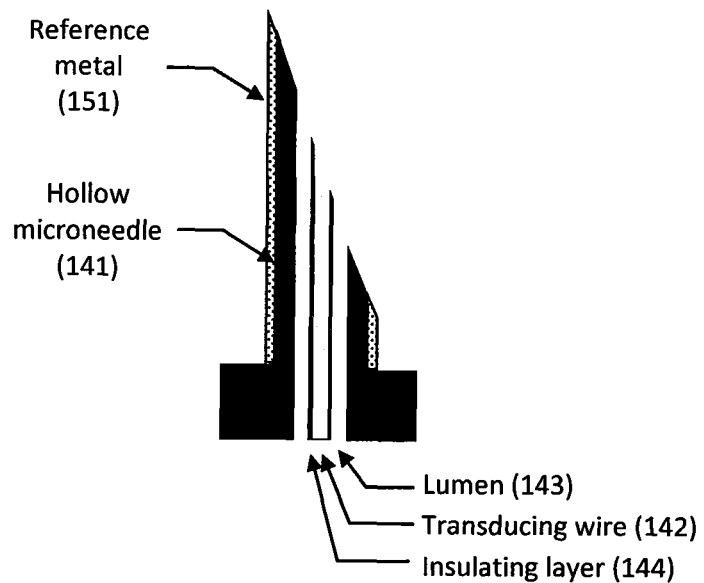
FIG. 12A shows a cross-sectional view of a hollow microneedle 141 coated with a reference material 151.

As shown in FIG. 12A, the needle 141 can, in some instances, provide a protective structure during insertion and can be used as a reference material in its native state or by coating 151 with another metal more commonly used in electrochemistry (e.g., a noble metal, such as silver, gold, or platinum).

Figure 12B:
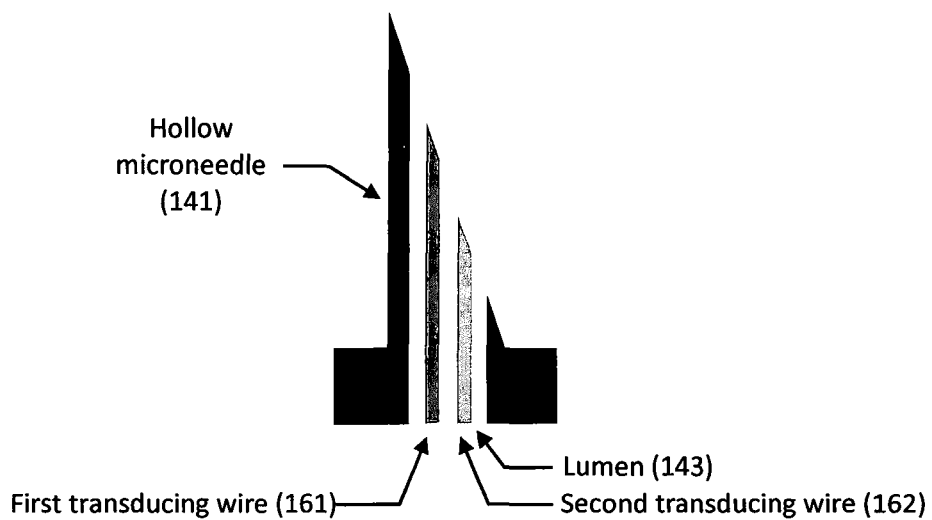
FIG. 12B shows a cross-sectional view of a hollow microneedle 141 comprising a first transducing wire 161 and a second transducing wire 162.

In this way, the transducing wire (e.g., an exposed surface at the distal end of the transducing wire) can be modified to detect a target of interest (e.g., a molecule, a biomolecule, or any described herein). Furthermore, due to the size of the wires, multiplexed detection is possible (e.g., by placing a plurality of transducing wires within a single microneedle). In another instance, a plurality of transducing wires can be inserted within the needle to provide an internal reference, a counter electrode, and/or an additional sensor for multiplexed detection. For example, as shown in FIG. 12B, the needle 141 can comprise a first transducing wire 161 and a second transducing wire 162 wherein each transducing wire provides a counter electrode, a reference electrode, or a working electrode.

The assembly can be formed in any useful manner. In one instance, the transducing wire is insulated with an insulating layer (e.g., any herein, such as parylene C, and in any useful manner, such as from a cathodic deposition bath), which deposits an insulating film (e.g., an insulating ceramic film) over the wire. In some non-limiting instances, the added rigidity from the insulating layer provides added rigidity to the wire, thereby easing handling and placement of the wire within the hollow microneedle. Once placed within the needle, the wire(s) can be adhered and trimmed, e.g., to provide a wire face in the same plane as the face of the needle. Further optional steps can include modifying the exposed surface of the transducing wire, e.g., by way of electrochemical modification, such that one or more enzymes are entrapped within a conducting polymer membrane disposed on the exposed surface of the wire. In another embodiment, the exposed surface of the wire can be coated with a monolayer of a surface bound capture agent that selectively reacts with the desired target.

The assembly can include any useful arrangement of needle(s) and transducing wire(s). Such an arrangement can be provided in any useful manner, such as a device (e.g., a laminate device). FIG. 2 provides an exploded view of an exemplary device 200. The device includes a plurality of layers 210-250 (e.g., layers formed from a polymer and/or an adhesive, such as any herein). The first layer 210 includes a positioning key 217, as well as an aperture 211 configured to include a microneedle array 201 disposed on a substrate 203. The array can include a plurality of needles, in which each needle includes a transducing wire inserted within the lumen of the needle (e.g., any described herein).

The second layer 220 is optionally an adhesive layer and includes a positioning key 227 (aligned to positioning key 217), a fluidic chamber 225 configured to be in fluidic communication with the hollow lumen of the microneedle array 201, and a fluidic channel 226 in fluidic communication with the fluidic chamber 225. In some embodiments, an adhesive layer is a layer including a substrate having a top surface and a bottom surface, as well as an adhesive composition disposed on the top surface and the bottom surface.

The third layer 230 can include one or more features to align and place one or more sensing transducers. As can be seen, this layer 230 includes a plurality of accesses 232, which are configured to place a sensing component (e.g., a sensing transducer, such as an electrical contact, a wire, or an electrode) in the fluidic path provided by within the fluidic chamber 225. In some non-limiting embodiments, each access is aligned to be in fluidic communication with one transducing wire within the array, thereby allowing a single sensing component to be in electrical contact with a single transducing wire, which in turn is disposed within the lumen of the needle. This third layer can also include an outlet 235 that is optionally configured to interface with a valve 236 and to be aligned with the fluidic channel 226, as well as a positioning key 237.

The fourth layer 240 can include a positioning key 247, an outlet 245 in fluidic communication with the outlet 235 in the third layer, and a plurality of accesses 241 in fluidic communication with the accesses 232 in the third layer. In some embodiments, the fourth layer is an adhesive layer (e.g., any described herein, such as a layer including a substrate having a top surface and a bottom surface, as well as an adhesive composition disposed on the top surface and the bottom surface).

The base layer 250 can include a positioning key 257, an outlet 255 in fluidic communication with the outlet 245 in the fourth layer, and a plurality of accesses 251 in fluidic communication with the accesses 241 in the fourth layer. The outlets and accesses in this base layer facilitates insertion of one or more contacts 251-253 and/or fluidic connectors 256. A skilled artisan would understand that additional modifications and design consideration can be implemented to achieve the desired fluidic network or path.

Needles and Transducing Wires

The device of the invention can have one or more needles and/or transducing wires of any useful dimension, such as length, width, height, circumference, and/or cross-sectional dimension. In particular, a skilled artisan would be able to optimize the needle length based on the type of fluid or type of tissue to be measured. For instance, the skin can be approximated as two layers including the epidermis (thickness of 0.05 to 1.5 mm) and the dermis (thickness of 0.3 to 3 mm). Accordingly, to obtain fluid in the dermis layer, the needle can be optimized to have a length that is more than about 0.3 mm, 0.5 mm, 1 mm, 1.5 mm, 2 mm, 2.5 mm, or 3 mm, depending on the desired location of the device on the body. A desired cross-sectional dimension can be determined by the skin site to be sampled (e.g., a dimension to allow for local testing of the subject, while minimizing pain), by the desired flow rate of the sample within the lumen of the needle (e.g., the flow rate can be optimized to allow for obtaining a fluid within a particular sampling time, or to minimize sample contamination, coagulation, and/or discomfort to the subject), by the desired volume of sample to be collected, etc.

The dimension of the transducing wire can be chosen to be compatible with the dimensions of the needle. For instance, if the transducing wire will be inserted within the lumen of the needle, then the width of the transducing wire can be less than the width of the lumen for the needle.

To access a sample within a subject, each needle can have one or more puncturing edges of any useful geometry. In some embodiments, the puncturing edge at the distal end of the needle includes a tapered point. In particular embodiments, the tapered point is located at the apex of a pyramidal needle, where the base of the needle is attached to the substrate and one side of the pyramidal needle is open, thereby forming the lumen of the needle. In yet other embodiments, the puncturing edge is a sharpened bevel for any useful geometrical shape forming the hollow needle, such as a cylinder, a cone, a post, a rectangle, a square, a trapezoid, as well as tapered forms thereof (e.g., a tapered cylinder or a tapered post), etc. In further embodiments, the puncturing edge includes one or more prongs (e.g., two, three, four, five, or more prongs) for obtaining a sample from a subject.

The needles can be formed from any useful material, e.g., a polymer (e.g., such as a biocompatible polymer; an acrylate-based polymer, such as e-Shell 200 (0.5-1.5% wt phenylbis(2,4,6 trimethylbenzoyl)-phosphine oxide photoinitiator, 15-30% wt propylated (2) neopentyl glycoldiacrylate, and 60-80% wt urethane dimethacrylate) or e-Shell 300 (10-25% wt urethane dimethacrylate and 10-20% tetrahydrofurfuryl-2-methacrylate); a resorbable polymer, e.g., polyglycolic acid (PGA), polylactic acid (PLA) including poly(L-lactide) (PLLA) and poly(D-lactide) (PDLA), or PGA-PLA copolymers; or any described herein), silicon, glass, a metal (e.g., stainless steel, titanium, aluminum, nickel, silver, gold, platinum, as well as alloys thereof, or any described herein), a conductive material (e.g., a noble metal or carbon fiber), a composite material, etc. The surface (e.g., interior and/or exterior surface) of the needle can be surface-modified with any agent described herein (e.g., a linking agent, capture agent, label, and/or porous material, as described herein). Additional surface-modified needles are described in U.S. Pub. No. 2011/0224515, as well as U.S. Pat. Nos. 7,344,499 and 6,908,453, each of which is incorporated by reference herein in its entirety. A surface of the needle can be modified to include a conductive material, such that the base material can be a non-conductive material that is then coated with a conductive material (e.g., any described herein, such as for a transducing wire). Exemplary needles are described in U.S. Pub. No. 2011/0224515; and Int. Pub. No. WO 2013/058879, each of which is incorporated by reference in its entirety.

The transducing wire can be formed from any useful material (e.g., a conductive material). Exemplary materials include gold, platinum, silver, carbon fiber, graphene, and/or indium tin oxide. In yet other embodiments, the working electrodes are chemically surface-modified to facilitate the bioassay. In various embodiments, the working electrodes are chemically surface-modified to facilitate immunoassay to detect one or more protein markers (e.g., troponin and/or myoglobin).

The needle and/or the transducing wire can include an insulating layer. The insulating layer can be formed from any useful material, as well as composites thereof, configured to provide electrical isolation. Exemplary insulating layers can include one or more ceramics (e.g., in any useful form, such as a nanoparticle), including but not limited to zirconia, silica, alumina, yttria, or magnesia); a ceramic within a resin (e.g., including one or more polymers, such as polyurethane, epoxy, and/or acrylic); a dielectric; or a polymer (e.g., parylene C). Exemplary composites include Ceramix (a nano-ceramic e-coating from Legor Group, S.p.A., Bressanvido, Italy), Nano Coating (a nano $SiO_2$ resin from Nanoshell LLC, Wilmington, Del.), and Nanocryl® (a nanocomposite including colloidal silica sol in various binders from Evonik Resource Efficiency GmbH, Essen, Germany).

Furthermore, a plurality of needles and/or transducing wires can be provided in an array. The array can include two, three, four, five, six, seven, eight, nine, ten, fifteen, twenty, or more needles and/or wires configured in any useful arrangement (e.g., geometrical arrangements). The array can have any useful spatial distribution of needles (e.g., a square, rectangular, circular, or triangular array), a random distribution, or the like.

The needle and/or transducing wire can contact any useful substance, e.g., any described herein, such as a conductive component. In particular embodiments, one or more needles or wires include a substance that further includes one or more capture agents. For example, the needle can include (e.g., within a portion of the lumen of the needle) a matrix including an electroactive component. The electroactive component can be, e.g., a carbon paste including one or more capture agents (e.g., an enzyme or a catalyst (e.g., rhodium) for detecting a marker). Further embodiments are described in Windmiller JR et al., "Microneedle array-based carbon paste amperometric sensors and biosensors," *Analyst* 2011; 136:1846-51, which is incorporated by reference in its entirety. Exemplary conductive components include a carbon paste, a conductive polymer (e.g., polyaniline, poly (bithiophene), polyaniline, or poly(pyrrole), such as dodecylbenzenesulfonate-doped polypyrrole), graphite, graphite powder, a metal, such as metal nanoparticles (e.g., gold, silver, platinum, and/or palladium nanoparticles), metal microparticles, a metal film (e.g., palladium or platinum), a nanotube, etc., which can optionally include an entrapped (e.g., enzyme) capture agent (e.g., any described herein).

Substrate

In general, a substrate refers to a substantially planar surface or media containing one or more structures. For instance, one or more needles, transducing wires, fluidic channels, transducers, fluidic component, sensor component, delivery component, and/or electronic component can be embedded in the same substrate or in different substrates. The substrate can be formed from any useful material. Exemplary materials include any described herein, such as a flexible substrate (e.g., a polyvinylacetate, a polyester, or any other described herein) or a printed circuit board (PCB).

The substrate can include one or more inlets in fluidic communication with the needle. In this manner, a sample collected within the needle can be delivered through the needle and into the inlet. Generally, the inlet is further configured to be in fluidic communication with one or more fluidic channels, as described herein.

When the substrate is the PCB, then one or more vias can be present for fluidic communication between the needle, transducing wire, and a pump (e.g., by way of a fluidic component or channel). In this way, pumps can be used to withdraw additional sample (e.g., a sample of interstitial fluid) into the needle manifold for monitoring and detecting one or more markers.

Other structures can be integrated into a substrate, such as, e.g., a filter, a permeable or semi-permeable membrane, a valve, and/or an electrode (e.g., any described herein).

Furthermore, the device of the invention can include multiple substrates (e.g., configured in multiple layers). For ease of manufacturing, the needles can be manufactured in a first substrate, other structures (e.g., fluidic channels and/or depots) can be included in a second substrate, and the transducer(s) can be included in a third substrate. An electronic component can be included as a fourth substrate (e.g., as a PCB substrate). Alternatively, the transducer(s) can be deposited on the PCB substrate. Then, the first, second, third, and fourth substrates, if present, are aligned (e.g., by including one or more registration marks or alignment holes on each substrate) and then laminated (e.g., by using an adhesive layer between substrate layers). A skilled artisan would be able to optimize manufacturing parameters for the particular design of the device and arrangement of these various structures.

Fluidic Channels, Chambers, and Depots

One or more fluidic channels (including inlets), chambers, and depots can be used to effect fluidic communication between two structures or regions. In particular embodiments, depots are fluidic chambers configured to store one or more therapeutic agents.

The present invention could also allow for integration between one or more needles with an array of depots. For instance, each needle can be associated with a particular depot, such that there is a one-to-one correspondence between the type of therapeutic agent being injected into the user and one particular needle. In other embodiments, each needle is associated with an array of depots. In yet other embodiments, an array of needles is associated with an individual depot or with an array of depots. The fluidic connection between the needle and the depots can be established by a channel or a network of channels.

Any of the fluidic channels, chamber, and depots described herein can be surface modified (e.g., to increase biocompatibility, decrease protein adsorption or absorption, and/or decrease surface contamination). Furthermore, such fluidic channels, chamber, and depots can also include one or more capture agents to selectively or non-selectively bind to cellular components or contaminants within a sample.

Surface Modification

Any of the surfaces described herein may be modified to promote biocompatibility, to functionalize a surface (e.g., using one or more capture agents including the optional use of any linking agent), or both. Exemplary surfaces include those for one or more needles, transducing wires, fluidic channels, depots, filters, and/or substrates (e.g., a PCB substrate).

The surface can be modified with any useful agent, such as any described herein. Exemplary agents include a capture agent (e.g., any described herein, such as an antibody); a polymer, such as a conducting polymer (e.g., poly(pyrrole), poly(aniline), poly(3-octylthiophene), or poly(thiophene)), an antifouling polymer, or a biocompatible polymer (e.g., chitosan), or a cationic polymer)); a coating, e.g., a copolymer, such as a copolymer of an acrylate and a lipid, such as butyl methacrylate and 2-methacryloyloxyethyl phosphorylcholine; a film; a label (e.g., any described herein); a linking agent (e.g., any described herein); an electroactive component, such as one or more carbon nanotubes or nanoparticles (e.g., gold, copper, cupric oxide, silver, or platinum nanoparticles), such as, for stabilizing an electrode; an enzyme, such as glucose oxidase, cholesterol oxidase, horse radish peroxidase, or any enzyme useful for oxidizing, reducing, and/or reacting with a marker of interest; or combinations thereof (e.g., an electroactive component coated with a polymer, such as a carbon nanotube coated with polyaniline).

Optionally, linking agents can be used be attach the agent to the surface. Exemplary linking agents include compounds including one or more first functional groups, a linker, and one or more second functional groups. In some embodiments, the first functional group allows for linking between a surface and the linker, and the second functional group allows for linking between the linker and the agent (e.g., a capture agent, a label, or any agent described herein). Exemplary linkers include any useful linker, such as polyethylene glycol, an alkane, and/or a carbocyclic ring (e.g., an aromatic ring, such as a phenyl group). In particular embodiments, the linking agent is a diazonium compound, where the first functional group is a diazo group ($-N_2$), the linker is an aryl group (e.g., a mono-, bicyclic, or multicyclic carbocyclic ring system having one or two aromatic rings and is exemplified by phenyl, naphthyl, xylyl, 1,2-dihydronaphthyl, 1,2,3,4-tetrahydronaphthyl, fluorenyl, indanyl, indenyl, and the like), and the second functional group is a reactive group for attaching a capture agent or a label (e.g., where the second functional group is halo, carboxyl, amino, sulfo, etc.). Such diazonium compounds can be used to graft an agent onto a surface (e.g., an electrode having a silicon, iron, cobalt, nickel, platinum, palladium, zinc, copper, or gold surface). In some embodiments, the linking agent is a 4-carboxybenzenediazonium salt, which is reacted with a capture agent by 1-ethyl-3-[3-dimethylaminopropyl]carbodiimide hydrochloride (EDC)/N-hydroxy succinimide (NHS) crosslinking, to produce a diazonium-capture agent complex. Then, this resultant complex is deposited or grafted onto a surface (e.g., an electrode surface).

Other exemplary linking agents include pairs of linking agents that allow for binding between two different components. For instance, biotin and streptavidin react with each other to form a non-covalent bond, and this pair can be used to bind particular components. A first capture agent can be an antibody attached to a substrate with a diazonium linking agent, a second capture agent can be an antibody labeled with biotin, and a third capture agent can be an enzyme labeled with streptavidin.

Platform

The present invention also includes a platform, which in turn includes a cartridge module (e.g., a disposable cartridge module) and a handheld module (e.g., a handheld detector module, diagnostic module, or acquisition module). In particular, the cartridge and handheld modules are designed to have matching configurations, thereby allowing the cartridge to be replaced with minimal effort by the user. The handheld module can be adapted for any useful purpose. For instance, when the platform is to be used for diagnosing or treating a disease or a medical condition, then the handheld module can include one or more detectors or electronic devices for real-time detection of one or more markers. Alternatively, when the platform is to be used for acquiring samples, then the handheld module can include one or more pumping mechanisms (e.g., active or passive pumps or pressure sources) to draw an obtained sample through the hollow microneedles and into the cartridge.

The platform can include a handheld module, which includes a body, and a cartridge module (e.g., a disposable cartridge). The handheld module can include one or more transducers and/or pumping mechanisms disposed within the body. In addition, the handheld module can be integrated with an electronic readout or, alternatively, can be configured to wirelessly communicate with an external device that provides such a readout (such as an electronic readout interface, including a smartphone, a cell phone, a mobile device, a mobile phone, etc.).

The body can include a central bore in fluidic communication with a disposable cartridge, one or more sensing transducers (e.g., a working electrode, a reference electrode, or any described herein), and a pumping mechanism (e.g., a vacuum source). The distal portion of the body can include a mounting shaft configured to interface with the disposable cartridge. The proximal portion of the body can include a handle, and the body can be configured to interface with an electronic readout interface, such as a smartphone, to control, e.g., the detector, the pumping mechanism, and/or release mechanism that detaches the cartridge from the handheld module.

The platform can include any useful structure(s) to affix the cartridge to the handheld module and then, after use, to release the cartridge for disposal for storage. For instance, the cartridge and handheld module can include one or more locking members and structures to position the cartridge at the distal end of the handheld module; sealing members and structures to ensure a fluidic seal between the modules, thereby containing the sample in a controlled manner; and/or release mechanisms to release the cartridge from the distal end of the handheld module. Exemplary cartridges and matching configurations for the handheld module are provided in FIG. 3 and FIG. 4A-4B.

Figure 3:
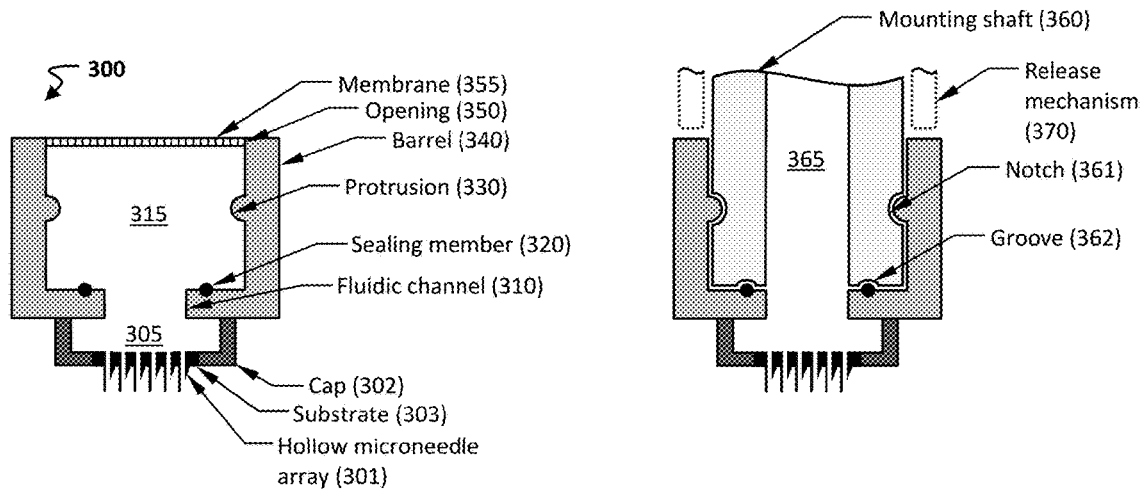
FIG. 3 shows schematics of an exemplary disposable cartridge 300 for use with a mounting shaft 360 of a handheld module.

FIG. 3 provides an exemplary cartridge 300 including a barrel 340 and a cap 302 configured to house the substrate 303 and microneedle array 301 (e.g., any described herein). The cap 302 is disposed at the distal end of the barrel 340, and an opening 350 is disposed at the proximal end of the barrel 340. In particular, the opening 350 is configured to interface with the handheld module (e.g., the mounting shaft of the handheld module) and can optionally include a frangible membrane 355 (e.g., to maintain sterility).

The barrel 340 includes an internal volume 315. When a cap is present, then the cap also has an internal volume 305 that is in fluidic communication with volume 315. Fluidic communication can be established by way of a fluidic channel 310. One or more structures can be present on a surface portion that defines the internal volume 315 of the barrel 340. Such structures include a locking member configured to affix the cartridge to the handheld module, as well as a sealing member to ensure a fluidic seal between the cartridge and the handheld module. An exemplary locking member includes a protrusion 330 which is located on a surface portion defining the internal volume 315, and this protrusion can either be a circumferential ring or a circular protrusion. An exemplary sealing member 320 includes, e.g., an o-ring, located on a surface portion defining the internal volume 315. A skilled artisan would understand how to place these structures to optimize locking and sealing, respectively.

The corresponding handheld module includes a mounting shaft that is configured to match the cartridge. As seen in FIG. 3, the mounting shaft 360 is disposed on the distal section of the body and includes a central bore 365 in fluidic communication with the cartridge. The mounting shaft is configured to be inserted into the opening 350 of the disposable cartridge 300 (e.g., any herein, including module forms thereof). The mounting shaft can include a fitting structure and/or a sealing structure disposed on an outer surface portion of the mounting shaft, where the fitting structure is configured to interface with the locking member of the disposable cartridge and where the sealing structure is configured to interface with the sealing member of the disposable cartridge. An exemplary fitting structure includes a notch 361 that is configured to interface with the protrusion 330 of the cartridge. An exemplary sealing structure includes a groove 362 that is configured to interface with the sealing member 320 of the cartridge. To facilitate release of the cartridge, the handheld module can optionally include one or more levers 370 that eject the cartridge 300 from the mounting shaft 360.

Figure 4A:
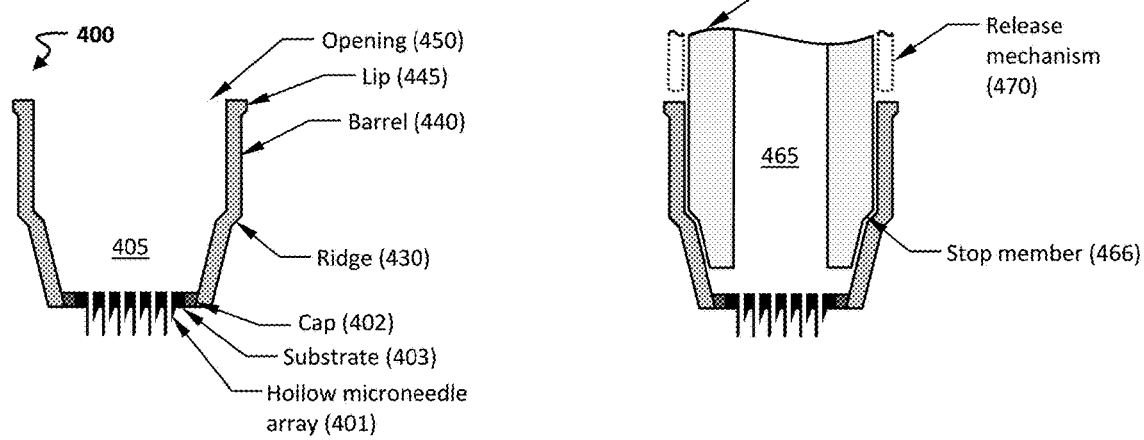
FIG. 4A-4B shows schematics of another exemplary disposable cartridge 400 for use with a mounting shaft 460 of a handheld module.
Figure 4B:
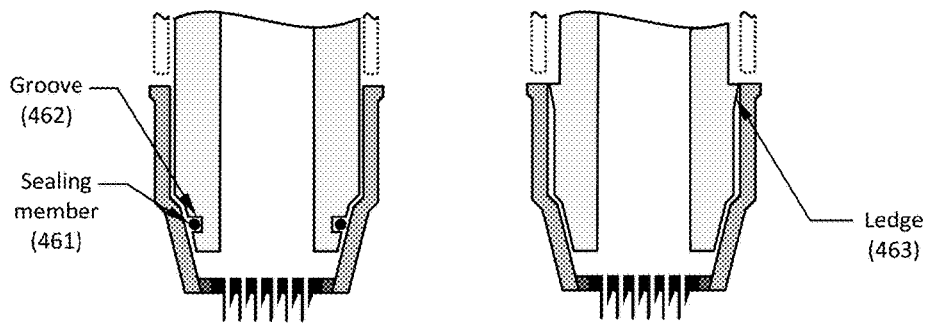
Figure 5A:
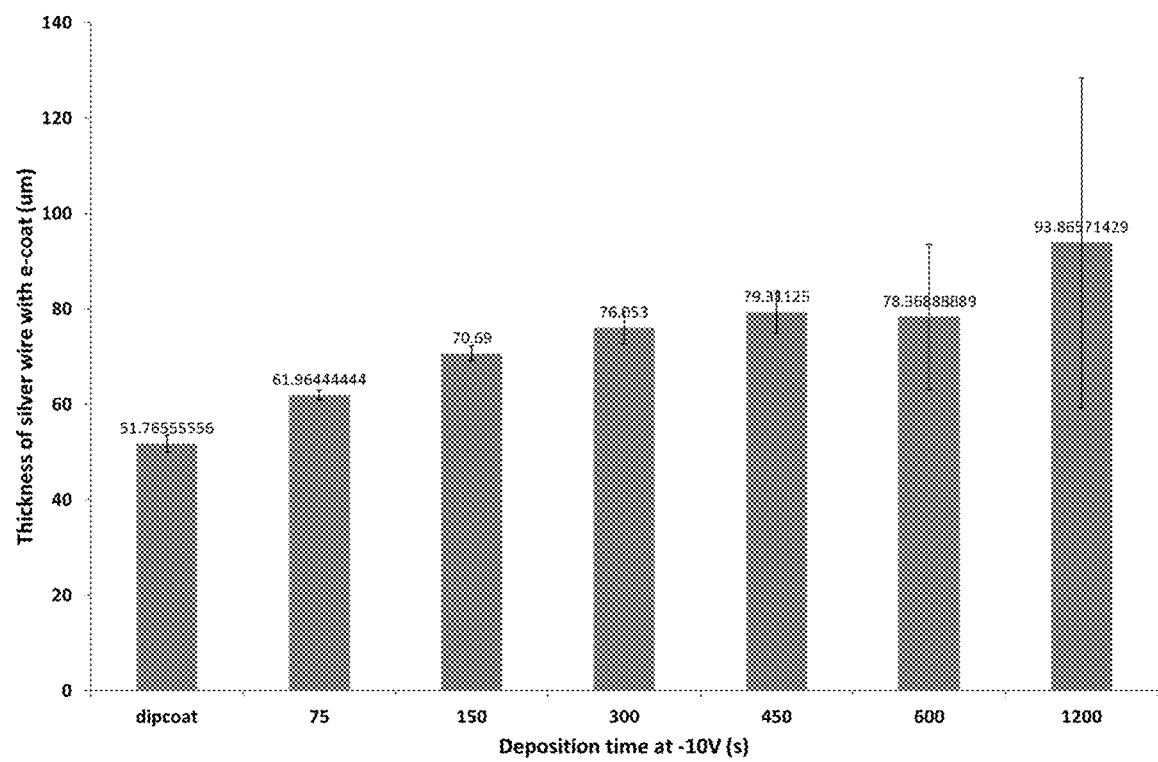
FIG. 5A-5B shows deposition of a ceramic resin on a 50 μm silver wire. Provided are a graph showing the effect of deposition time on the thickness of the wire having a coating of the ceramic resin (FIG. 5A) and representative images of the wire for various deposition times (FIG. 5B).
Figure 5B:
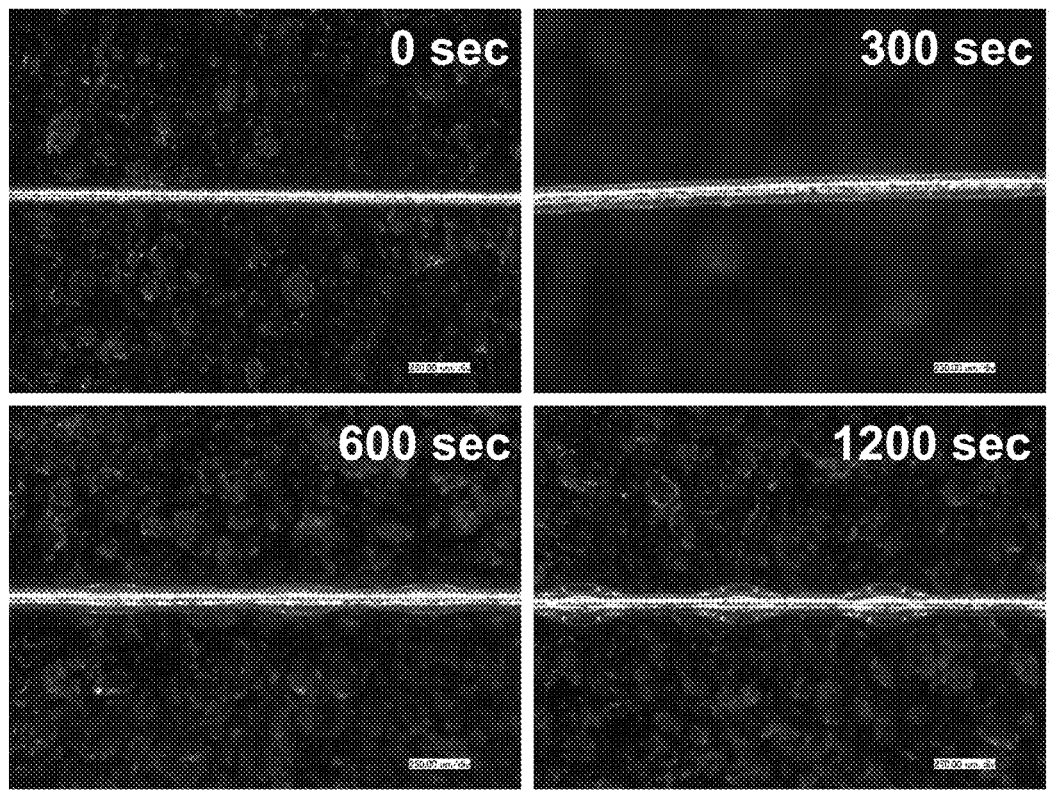

FIG. 4A-4B provides another exemplary cartridge 400 and its corresponding handheld module. The cartridge 400 includes a barrel 440 and a cap 402 configured to house the substrate 403 and microneedle array 401. The cap 402 is disposed at the distal end of the barrel 440, and an opening 450 is disposed at the proximal end of the barrel 440. Again, the opening can optionally include a frangible membrane (e.g., to maintain sterility).

The barrel 440 includes an internal volume 405. One or more structures can be present on a surface portion that defines the internal volume 405 of the barrel 440. Here, the exemplary locking member includes a ridge 430 which is located on a surface portion defining the internal volume 405, and this ridge can either be disposed circumferentially or disposed in one particular cross-sectional location. The ridge can optionally also serve as a sealing member. As can be seen, the corresponding mounting shaft 460 includes a central bore 465 in fluidic communication with the cartridge, as well as a stop member 466 that interfaces with the ridge 430 of the cartridge.

The handheld module can include other structural attributes for the mounting shaft, as seen in FIG. 4A-4B. For instance, the mounting shaft can include an additional sealing structure, such as a groove 462 configured to align a sealing member 461 (e.g., an o-ring) with a surface portion defining the internal volume 405 of the cartridge. In another embodiment, the mounting shaft can include a locking member or a sealing member that is a ledge 463, which interfaces with the lip 445 of the cartridge 400, thereby stabilizing the module interface and minimizing fluid leakage. Optionally, the handheld module can optionally include a release mechanism 470 (e.g., one or more levers).

The handheld module and disposable cartridge can be employed in any useful manner. In one instance, the handheld module can be used to affix the cartridge to the desired site (e.g., a sample site for the subject). Then, the handheld module can be activated to either perform a measurement and/or to actuate a pumping mechanism. Finally, the cartridge can be released from the handheld module after either obtaining a measurement (e.g., detecting the presence or absence of one or more markers) or acquiring the sample.

Alternatively, obtaining a sample may take an extended period of time (e.g., more than 5 seconds, 10 seconds, 20 seconds, 30 seconds, 1 minute, etc.). In particular embodiments, such acquisition times can be optimized to ensure sufficient flow of the sample, while minimizing pain and discomfort to the subject. When extended acquisition times are needed, then the handheld module can be employed to apply the disposable cartridge and then detach the cartridge from the handheld module. In this way, the cartridge could collect sufficient fluid for analysis while the handheld module applies cartridge to other patients, thus gaining the ability to treat more patients. Once the cartridge has a suitable amount of fluid, the handheld module could be re-attached to the cartridge in order to perform a measurement.

Additional Components

The present device can include any useful additional component. Exemplary components include those provided for a transducer (e.g., any described herein, as well as those in Justine. CIL et al., "Review of analytical figures of merit of sensors and biosensors in clinical applications," *Trends Analyt. Chem.* 2010; 29:1172-83, which is incorporated by reference in its entirety); those provided for a microneedle (e.g., any described herein, as well as those in Gittard S D et al., "Two photon polymerization of microneedles for transdermal drug delivery," *Exp. Opin. Drug Deliv.* 2010; 7(4):513-33, and Miller P R et al., "Multiplexed microneedle-based biosensor array for characterization of metabolic acidosis," *Talanta* 2012; 88:739-42, each of which is incorporated by reference in its entirety); a membrane (e.g., placed between the needle and the channel; placed within a channel, such as to filter one or more particles within the sample; and/or placed between the channel and the electrode); a multifunctional sensor (e.g., to measure temperature, strain, and electrophysiological signals, such as by using amplified sensor electrodes that incorporate silicon metal oxide semiconductor field effect transistors (MOSFETs), a feedback resistor, and a sensor electrode in any useful design, such as a filamentary serpentine design); a microscale light-emitting diode (LEDs, such as for optical characterization of the test sample); an active/passive circuit element (e.g., such as transistors, diodes, and resistors); an actuator; a wireless power coil; a device for radio frequency (RF) communications (e.g., such as high-frequency inductors, capacitors, oscillators, and antennae); a resistance-based temperature sensor; a photodetector; a photovoltaic cell; and a diode, such as any described in Kim D et al., *Science* 2011; 333:838-43, which is incorporated herein by reference. These components can be made from any useful material, such as, e.g., silicon and gallium arsenide, in the form of filamentary serpentine nanoribbons, micromembranes, and/or nanomembranes.

The present device can include one or more structural components within the integral platform or substrate. Exemplary components include a mixing chamber in fluidic communication with the lumen of a needle; a reservoir optionally including one or more reagents (e.g., any described herein), where the reservoir can be in fluidic communication with the mixing chamber or any fluidic channel; a cell lysis chamber (e.g., configured to lyse one or more cells in a sample and in fluidic communication with needle and the sensing transducer); a controllable valve (e.g., configured to release a reagent from a reservoir into a mixing chamber); a pump (e.g., configured to facilitate flow of a sample to the transducer and/or through one or more fluidic channels); a waste chamber (e.g., configured to store a sample after detection of one or more reagents); a probe; and/or a filter (e.g., configured to separate one or more components from the sample either before or after detection with the transducer).

In some embodiments, the needle can be configured to be in fluidic communication with a reservoir (e.g., containing a drug for delivery and/or a reagent for detecting the marker of interest). Such a configuration can optionally include a valve between the needle and reservoir. In other embodiments, a probe can be configured to be in fluidic communication with the lumen of the needle. Exemplary needles and probes are described in Int. Pub. No. WO 2013/058879 (e.g., in FIG. 1A-1D, FIG. 1L, FIG. 2A-2C, FIG. 5A-5D, FIG. 12A-12B, FIG. 17, FIG. 18A-18D, and its related text), which is incorporated herein in its entirety.

The device can include one or more components to operate a transducer. For instance, in some embodiments, the transducer is an electrode or an array of electrodes. Accordingly, the device can further include a power source to operate the electrode. In particular embodiments, the device includes a data-processing circuit powered by the power source and electrically connected to the transducer (e.g., a counter electrode, a reference electrode, and at least one said working electrode). In further embodiments, the device includes a data output port for the data-processing circuit. Such data from the transducer can include any useful information, such as electromotive force (EMF), potentiometric, amperometric, impedance, and/or voltammetric measurements. Other data can include fluorometric, colorimetric, optical, acoustic, resonance, and/or thickness measurements.

The present invention can be useful for autonomous remote monitoring of a subject. The device of the invention can be placed on the skin of a subject, and the presence or absence of one or more markers can be remotely relayed to a heath care worker. Accordingly, the device described herein can include one or more components that would allow for such relay. Exemplary components include an analog-to-digital converter, a radiofrequency module, and/or a telemetry unit (e.g., configured to receive processed data from a data-processing circuit electrically connected to the transducer and to transmit the data wirelessly). In various embodiments, the telemetry unit is fixed within the platform or packaged separately from the platform and connected thereto by a cable.

Multiple Reactions

The present device can be used to perform multiple reactions on-chip. Such reactions can include those to prepare a sample (e.g., to dilute, concentrate, or filter a sample), to bind the sample to a capture agent, to prepare one or more reagents to be reacted with the sample (e.g., to reconstitute a reagent on-chip prior to reacting with the sample), to react the sample with any useful reagent, to store the sample on-chip, and/or to perform other post-processing reactions. To perform multiple reactions, the microneedles, fluidic channels, and transducers can be provided in an array format, such as any described herein.

To allow for multiple reactions or processing steps, the device can include additional chambers in fluidic communication with one or more needles. In one embodiment, the device includes one or more mixing chambers in fluidic communication with one or more needles and configured to receive the sample or a portion thereof. The mixing chamber can include one or more reagents (e.g., any described herein), buffers, diluents (e.g., water or saline), salts, etc. Optionally, the mixing chamber can include one or more components to assist in mixing, such as one or more of the following: a bead, a passive mixer, a rotary mixer, a microbubble, an electric field to induce electrokinetic and/or dielectrophoretic flow, a staggered structure to induce chaotic advection, an acoustic mixer, a heater to induce a thermal gradient, and/or a magnetic bead for use with a magnetic field generator.

The device can also include one or more reaction chambers (e.g., to combine one or more reagents (e.g., one or more enzymes and/or beads) within this chamber and/or to incubate reaction mixtures including the sample or a portion thereof), lysing chambers (e.g., to lyse one or more cells within the sample), washing chambers (e.g., to wash one or more components within the sample), elution or extraction chambers (e.g., including one or more filters, particles, beads, sieves, or powders to extract one or more components from the sample), and/or collection chambers (e.g., to collect one or more processed samples or aliquots thereof). In particular embodiments, at least one reaction chamber is in fluidic communication with at least one mixing chamber by a channel. In further embodiments, the reaction chamber is in fluidic communication two or more mixing chambers, thereby combining the substance in each mixing chamber within the reaction chamber. In this manner, parallel or serial sequences of substances can be combined in a controlled manner within a reaction chamber or multiple reaction chambers. A skilled artisan would be able to design arrays of mixing and/or reaction chambers (optionally interconnected with channels) to effect the proper sequence of each reaction step.

Any of the chambers and channels interconnecting such chambers can be surface modified, as described herein. Furthermore, such chambers and channels can include further structures that would be useful for detecting one or more markers. For instance, one or more filters or membranes can be used to separate particular components from the sample and/or the reaction mixture. For instance, when the sample is whole blood, a filter can be used to separate the plasma from other blood components, such as the red blood cells.

Test Samples

The present device can be used to test any useful test sample, such as blood (e.g., whole blood), plasma, serum, transdermal fluid, interstitial fluid, sweat, intraocular fluid, vitreous humor, cerebrospinal fluid, extracellular fluid, lacrimal fluid, saliva, mucus, etc., and any other bodily fluid.

The sample can be obtained from any useful source, such as a subject (e.g., a human or non-human animal), a plant (e.g., an exudate or plant tissue, for any useful testing, such as for genomic and/or pathogen testing), an environment (e.g., a soil, air, and/or water sample), a chemical material, a biological material, or a manufactured product (e.g., such as a food or drug product).

Substances, Including Reagents and Therapeutic Agents

The present device can further be adapted to deliver one or more substances from a reservoir to another region of the device or to a subject. In some embodiments, the device includes one or more reservoirs including a substance for detecting one or more markers of interest. Exemplary substances include a reagent (e.g., any described herein, such as a label, an antibody, a dye, a capture agent, etc.), a buffer, a diluent, a salt, etc.

In other embodiments, the device includes one or more substances that can be injected or delivered to a subject (e.g., one or more therapeutic agents). Such therapeutic substances include, e.g., an analgesic, anesthetic, antiseptic, anticoagulant, drug (e.g. adrenaline and/or insulin), vaccine, medical countermeasure, etc.

Capture Agents

Any useful capture agents can be used in combination with the present invention. The capture agent can directly or indirectly bind the marker of interest. Further, multiple capture agents can be used to bind the marker and provide a detectable signal for such binding. For instance, multiple capture agents are used for a sandwich assay, which requires at least two capture agents and can optionally include a further capture agent that includes a label allowing for detection.

Exemplary capture agents include one or more of the following: a protein that binds to or detects one or more markers (e.g., an antibody or an enzyme), a globulin protein (e.g., bovine serum albumin), a peptide, a nucleotide, a nanoparticle, a microparticle, a sandwich assay reagent, a catalyst (e.g., that reacts with one or more markers), and/or an enzyme (e.g., that reacts with one or more markers, such as any described herein). The capture agent can optionally include one or more labels, e.g. any described herein. In particular embodiments, more than one capture agent, optionally with one or more linking agents, can be used to detect a marker of interest. Furthermore, a capture agent can be used in combination with a label (e.g., any described herein) to detect a maker.

Labels

The present device can include any useful label. The label can be used to directly or indirectly detect a marker. For direct detection, the label is conjugated to a capture agent that binds to the marker. For instance, the capture agent can be an antibody that binds the marker, and the label for direct detection is a nanoparticle attached to the capture agent. For indirect detection, the label is conjugated to a second capture agent that further binds to a first capture agent. A skilled artisan would understand how to optimize combinations of labels, capture agents, and linking agents to detect a marker of interest.

Exemplary labels include one or more fluorescent labels, colorimetric labels, quantum dots, nanoparticles, microparticles, barcodes, radio labels (e.g., RF labels or barcodes), avidin, biotin, tags, dyes, an enzyme that can optionally include one or more linking agents and/or one or more dyes, as well as combinations thereof etc.

Markers, Including Targets

The present device can be used to determine any useful marker or targets. Exemplary markers include one or more physiologically relevant markers, such as glucose, lactate, pH, a protein (e.g., myoglobin, troponin, insulin, or C-reactive protein), an enzyme (e.g., creatine kinase), a catecholamine (e.g., dopamine, epinephrine, or norepinephrine), a cytokine (e.g., TNF-α or interleukins, such as IL-6, IL-12, or IL-1β), an antibody (e.g., immunoglobulins, such as IgA), a biomolecule (e.g., cholesterol or glucose), a neurotransmitter (e.g., acetylcholine, glutamate, dopamine, epinephrine, neuropeptide Y, or norepinephrine), a signaling molecule (e.g., nitric oxide), an antigen (e.g., CD3, CD4, or CD8), an ion (e.g., a cation, such as $K^+$, $Na^+$, $H^+$, or $Ca^+$, or an anion, such as $Cl^-$ or $HCO_3^-$), $CO_2$, $O_2$, $H_2O_2$, a cancer biomarker (e.g., human ferritin, carcinoembryonic antigen (CEA), prostate serum antigen, human chorionic gonadotropin (hCG), diphtheria antigen, or C-reactive protein (CRP)), a hormone (e.g., hCG, epinephrine, testosterone, human growth hormone, epinephrine (adrenaline), thyroid hormone (e.g., thyroid-stimulating hormone (TSH), thyroxine (TT4), triiodothyronine (TT3), free thyroxine (FT4), and free triiodothyronine (FT3)), adrenal hormone (e.g., adrenocorticotrophic hormone (ACTH), cortical hormone (F), and 24-hour urine-free cortisol (UFC)), a gonadal hormone (e.g., luteinizing hormone (LH), follicle-stimulating hormone (FSH), testosterone, estradiol (E2), and prolactin (PRL)), cortisol, leptin, or a peptide hormone, such as insulin), an inflammatory marker (e.g., CRP), a disease-state marker (e.g., glycated hemoglobin for diabetes or markers for stress or fatigue), a cardiovascular marker (e.g., CRP, D-dimer, troponin I or T), a blood marker (e.g., hematocrit, or hemoglobin), a cell (e.g., a leukocyte, neutrophil, B-cell, T-cell, lymphocyte, or erythrocyte), a viral marker (e.g., a marker for human immunodeficiency virus, hepatitis, influenza, or chlamydia), a metabolite (e.g., glucose, cholesterol, triglyceride, creatinine, lactate, ammonia, ascorbic acid, peroxide, potassium, glutamine, or urea), a nucleic acid (e.g., DNA and/or RNA for detecting one or more alleles, pathogens, single nucleotide polymorphisms, mutations, etc.), an amino acid (e.g., glutamine), a drug (e.g., a diuretic, a steroid, a growth hormone, a stimulant, a narcotic, an opiate, etc.), etc. Other exemplary markers include one or more pathogens, such as *Mycobacterium tuberculosis*, *Diphtheria* antigen, *Vibrio cholera*, *Streptococcus* (e.g., group A), etc.

In particular embodiments, the marker is indicative of exhaustion (e.g., exercise-induced exhaustion) and/or fatigue (e.g., severe fatigue, such as in deployed military personnel). Such markers include, e.g., ACTH, ascorbic acid, CD3, CD4, CD8, CD4/CD8, cholesterol, cortical hormone, cortisol, creatine kinase, E2, epinephrine, FSH, FT3, FT4, glucose, glutamine, glutamate, hematocrit, hemoglobin, human growth hormone, IgA, insulin, insulin-like growth factor, interleukin-6, iron, lactate (e.g., serum or blood lactate), leptin, LH, neuropeptide Y, norepinephrine, peroxide, pH, potassium, PRL, TSH, TT3, TT4, testosterone, and/or urea.

Methods and Use

The present device can be applied for any useful method and/or adapted for any particular use. For instance, point-of-care (POC) diagnostics allow for portable systems, and the device herein can be adapted for POC use. In some embodiments, the device for POC use includes a test sample chamber, a microfluidic processing structure (e.g., any structure described herein, such as a needle, a substrate, and/or a channel), a target recognition region (e.g., including any transducer described herein), an electronic output, a control (e.g., a positive and/or negative controls), and/or a signal transduction region. Exemplary POC devices and uses are described in Gubala V et al., "Point of care diagnostics: status and future," *Anal Chem.* 2012; 84(2):487-515, which is incorporated by reference in its entirety. Such POC devices can be useful for detecting one or more markers for patient care, drug and food safety, pathogen detection, diagnostics, etc.

Wearable sensors are a new paradigm in POC devices, allowing for minimally invasive monitoring of physiological functions and elimination of biological fluid transfer between subject and device; these devices can be capable of providing real-time analysis of a patient's condition. In other embodiments, the device is adapted to include one or more components allowing for a wearable sensor. Exemplary wearable sensors, as well as relevant components, are described in Windmiller J R et al., "Wearable electrochemical sensors and biosensors: A review," *Electroanalysis* 2013; 25:29-46. Such components include a telemetry network including one or more devices (e.g., as described herein), one or more flexible substrates (e.g., where one or more transducers are integrated into a flexible substrate, such as cloth, plastic, or fabric, e.g., Gore-Tex®, an expanded polytetrafluoroethylene (ePTFE), polyimide, polyethylene naphthalate, polyethylene terephthalate, biaxially-oriented polyethylene terephthalate (e.g., Mylar®), or PTFE), and/or one or more flexible electrodes (e.g., a screen printed electrode printed on a flexible substrate, such as any herein).

In some embodiments, the device of the invention is adapted as an epidermal electronic device. Such devices can include, e.g., one or more printed flexible circuits that can be stretched and bent to mimic skin elasticity can perform electrophysiological measurements such as measuring temperature and hydration as well as monitoring electrical signals from brain and muscle activity. Exemplary components for such a device are described in Kim D et al., *Science* 2011; 333:838-43, which is incorporated herein by reference.

In other embodiments, the device of the invention is adapted as a temporary tattoo. Such tattoos can include, e.g., one or more screen printed electrodes directly attached to the skin were recently reported to measure lactate through sweat. Exemplary components for such a device are described Jia W et al., "Electrochemical tattoo biosensors for real-time noninvasive lactate monitoring in human perspiration," *Anal. Chem.* 2013; 85:6553-60, which is incorporated herein by reference.

The device of the invention can be configured for any useful method or treatment. For instance, the device can be configured for locally treating, delivering, or administering a therapeutic substance after detecting one or more markers. Exemplary methods and devices are described in Int. Pub. No. WO 2010/022252, which is incorporated herein by reference.

Kits

The present device can be provided in any useful form, such as in a kit. In some embodiments, the device is provided in combination with an adhesive layer and a backing liner, where peeling of the backing liner exposes the adhesive layer and allows for positioning the device on the skin of a subject. In other embodiments, the kit includes a device (e.g., any described herein), an instruction for use, and, optionally, one or more therapeutic agent (e.g., any described herein).

Packaged Chip

The present device can be provided in any useful package. For instance, such a package can include a packaged chip having a housing for the device of the invention. In one embodiment, the housing includes a substantially planar substrate having an upper surface and an opposing lower surface; a first fluidic opening disposed on the upper surface of the substrate; a second fluidic opening disposed on the lower surface of the substrate; a first fluidic channel fluidically connecting the first fluidic opening to the second fluidic opening; and a first adhesive layer adhered to the upper surface, having a hole disposed through the layer, wherein the hole is substantially aligned with, and fluidically coupled to, the first fluidic opening in the substrate. In some embodiments, the housing includes one or more structures allowing for integrating with a fluidic printed wiring board having a standard electrical printed circuit board and one or more fluidic channels embedded inside the board. An exemplary packaged chip is provided in U.S. Pat. No. 6,548,895, which is incorporated by reference in its entirety. Further components for a packaged chip include a substrate including an electrically insulating material, one or more electrical leads, a substantially planar base, an external fixture, etc., as well as any other components described in U.S. Pat. Nos. 6,443,179 and 6,548,895, each of which is incorporated herein by reference in its entirety.

The device of the invention can be provided in any useful format. For instance, the device can be provided with particular components integrated into one package or monolithic structure. A non-limiting example of such an integrated device is provided in FIG. 1A, where the needles, fluidics, and electrode array are provided in an integrated format. In other examples, the device is provided as a modular package, in which the needles, fluidics, and electrodes are provided as separate plug-and-play modules that can be combined. In particular embodiments, a sensor module includes a packet of electrode arrays with each packet containing specific chemistries. In further embodiments, the sensor module is configured to be relevant for the desired analyte, such as to detect a particular drug or a particular virus. Further modules can include a needle module including one or more needles (e.g., an array of needles); a fluidics module including one or more chambers, valves, and/or channels; a delivery module including one or more therapeutic agents; and/or a reagent module including one or more prepackaged reagents and buffers configured for a particular test or analyte. Such modules can be reusable or disposable. For instance, if the sample processing is extensive, one would want a reusable fluidics module, which is configured for fluidic communication with the needle module and sensor module. In further embodiments, the needle and sensor modules can be disposable. In another example, if sample processing or sensing requires an elaborate needle (e.g., a needle having a particular geometrical configuration and/or surface modification), then the needle module can be configured to be reusable. Other considerations include possibility of contamination of one or more modules, etc. A skilled artisan would understand how modules can be configured for fluidic communication with other modules and designed for reusability or disposability.

EXAMPLES

Example 1

Fabrication of an Exemplary Coaxial Needle Assembly

An exemplary coaxial needle assembly was fabricated, in which the transducing wire was first insulated and then inserted into the lumen of a hollow needle. The transducing wire was insulated to reduce electrical contact with the needle and then modified by depositing a conductive component. Such a conductive component can allow for, e.g., entrapment of a capture agent, which in turn can allow for detection of a target analyte that interacts with the capture agent. Additional details follow.

First, silver metal wires were insulated prior to insertion into a pen needle. Cathodic deposition of a ceramic was investigated. A negative potential was applied to the wire to attract the ceramic particles, which created a film on the surface of the wire. Post-baking was employed to cure the film and seal the wire. Deposition time can be employed to control the thickness of the deposited insulator coating (see, e.g., FIG. 5A-5B).

Figure 6A:
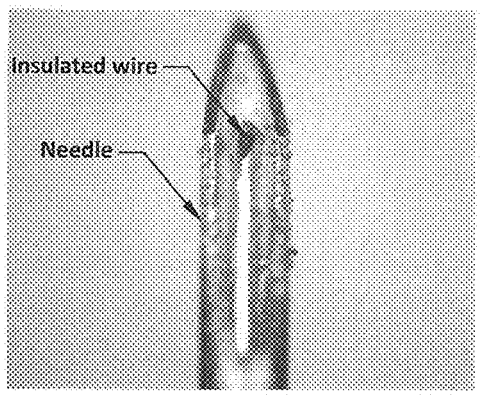
FIG. 6A-6B shows placement of an exemplary transducing wire (50 μm gold wire insulated with ceramic) within a hollow needle (a pen needle having an outer diameter of about 230 μm). Provided are front view (FIG. 6A) and profile view (FIG. 6B) images of the assembly.
Figure 6B:
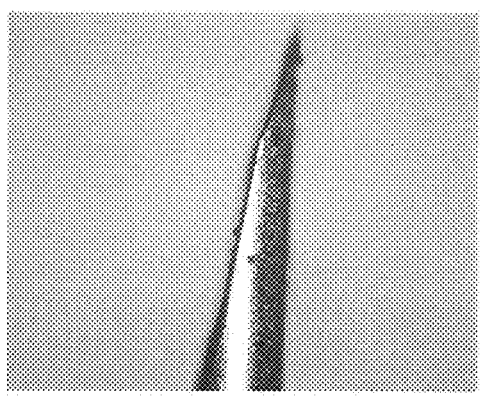

Then, the insulated wire was placed within the needle. Any useful metal wire (e.g., Au, Ag, Pt, carbon fiber, etc.) can be used to as transducers for biosensor development. In FIG. 6A-6B, the transducing wire was an insulated Au wire, which was then placed within a pen needle. The wire was inserted and sealed in position within the needle, then trimmed such that the exposed wire and needle face are in the same plane.

The wire insulation and assembly process allowed the wire and the needle to be electrically isolated. In some non-limiting instances, multiple wires can be inserted and electrically isolated, which could allow for single needle multiplexing or use of a more traditional reference material (e.g., Ag).

Figure 7A:
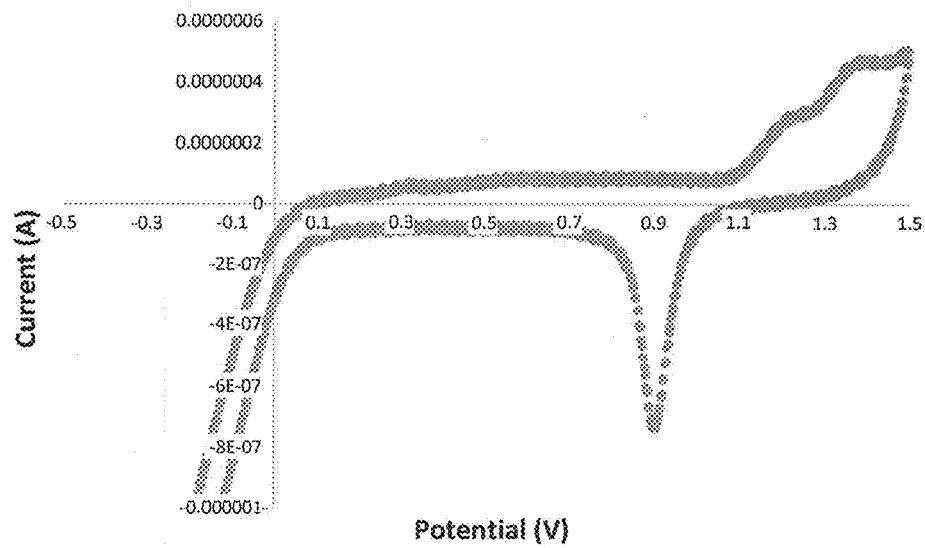
FIG. 7A-7B shows electrochemical traces of an exemplary transducing wire (50 μm gold wire). Provided are a characteristic cyclic voltammogram of a gold wire cycled in sulfuric acid (FIG. 7A) and a trace showing electrochemical growth of polyaniline on a gold wire (FIG. 7B, arrows indicate polymer film growth).

In some instances, cleaning of the transducing wire may be required, especially if further modifications are contemplated. In particular embodiments, transducing wire within a needle can be cleaned prior to deposition of a conductive component. FIG. 7A shows a characteristic cyclic voltammogram of a gold wire cycled in sulfuric acid, which is a standard cleaning procedure prior to biosensor development. This result indicates the supplier provides a suitable source for electrode material.

Figure 7B:
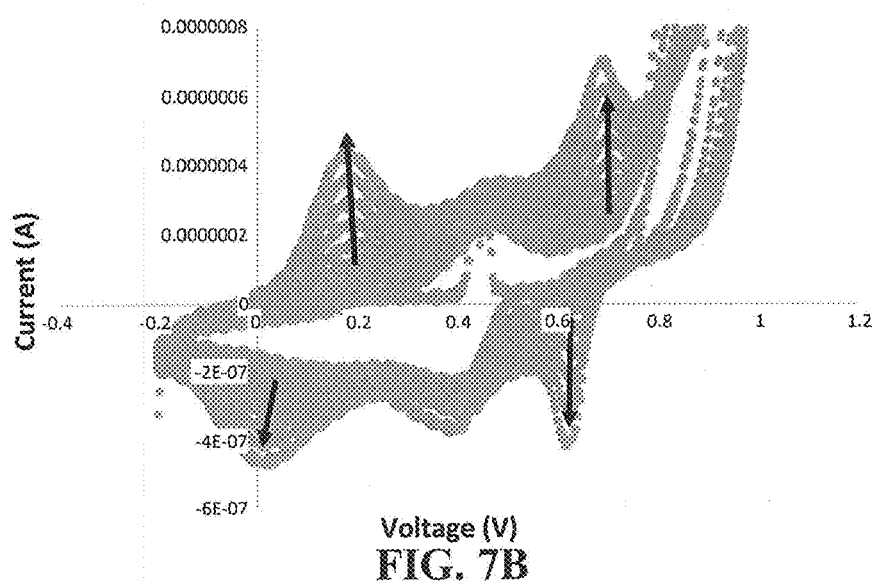

Further modifications to the cleaned transducing wire can include, e.g., deposition of a conductive polymer (e.g., polyaniline) and entrapment of an enzyme (e.g., lactate oxidase for detection of lactate as the target analyte) within that conductive polymer. Deposition can occur via oxidative polymerization at the electrode surface. FIG. 7B shows the electrochemical growth of polyaniline (conducting polymer) on a 50 µm diameter gold electrode. Future steps can include entrapping of lactate oxidase within deposited polyaniline, thereby allowing for detection of lactate.

Example 2

Characterization of a Coaxial Sensor for Hydrogen Peroxide

Initial studies were conducted for a coaxial sensor and its response to hydrogen peroxide, a by-product of lactate detection in the presence of lactate oxidase (LOx), an enzyme. LOx can be employed for enzymatic detection of lactate. In brief, LOx reacts with lactate and oxygen ($O_2$) to form hydrogen peroxide ($H_2O_2$), a reactive oxygen species that can be detected electrochemically (e.g., by use of voltammetric detection with electrodes). Thus, an exemplary biosensor can include use of LOx within a conductive component (e.g., a conductive polymer), which in turn is in electrical contact with the transducing wire. When LOx reacts with in situ lactate, $H_2O_2$ will be generated, and the resultant changes in potential be measured by use of the transducing wire. The following example details sensing of $H_2O_2$ with a coaxial sensor.

Figure 8:
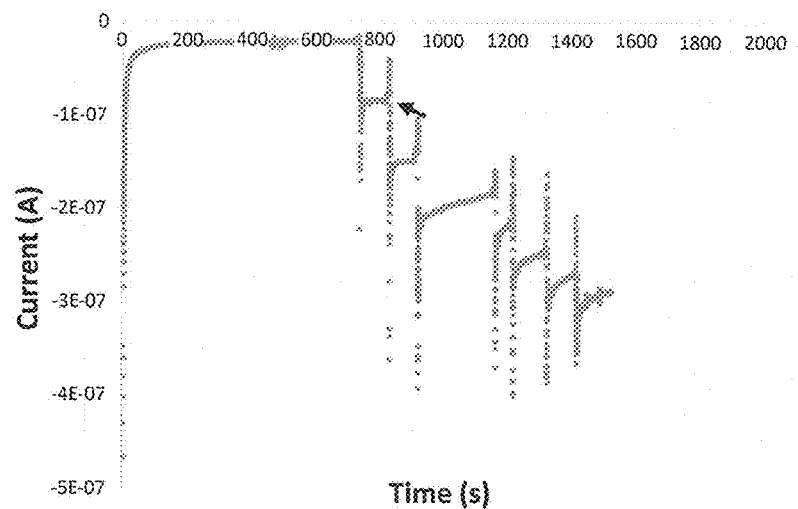
FIG. 8 shows an electrochemical trace of the response of a hollow needle to hydrogen peroxide ($H_2O_2$). The arrow indicates spike of 133 μM $H_2O_2$.

The needle was intended to serve as a structural housing for the biosensor. Thus, testing proceeded by applying a reducing potential to the needle, thereby reducing the peroxide present in the sample. This test is similar to that for detecting lactate by-products. FIG. 8 provides the needle response to $H_2O_2$, in which a fixed potential (−0.2V) was applied to the needle in the presence of a Ag/AgCl reference electrode and a Pt wire counter electrode (1× PBS, pH 7.2). As can be seen, the needle (without an insulating layer) reacts with the peroxide test solution, thereby causing false readings. Insulation of the needle can ensure that only the transducing wire will electrochemically interact with the test analyte and that the needle will remain electrochemically inactive.

Figure 9A:
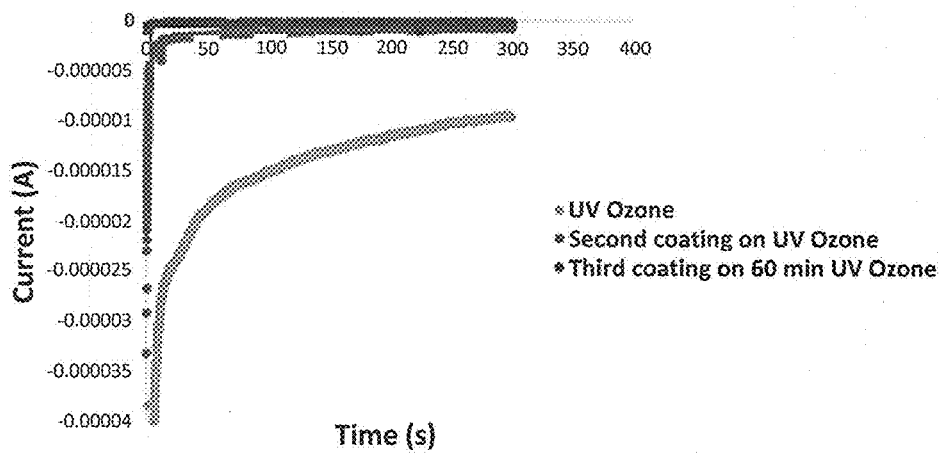
FIG. 9A-9B shows electrochemical characterization of an insulated hollow needle. Provided are electrochemical traces of a needle before and after insulation (FIG. 9A) and the response of an insulated hollow needle to $H_2O_2$ (FIG. 9B, arrow indicates spike of 133 μM $H_2O_2$).
Figure 9B:
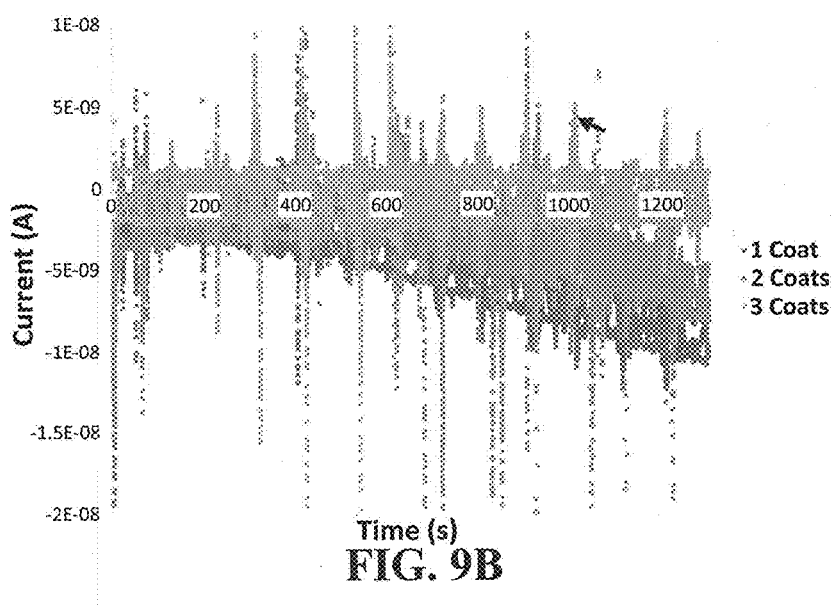

Electrical passivation experiments were then conducted. In brief, insulating layers were deposited on the needle, and its electrochemical response was determined. FIG. 9A shows electrodeposition of a ceramic resin on a needle at −10V. Repeating the deposition process provided additional coating of the needle and further insulation of the needle. FIG. 9B provides the needle response to $H_2O_2$, in which a fixed potential (−0.2V) was applied to the needle in the presence of a Ag/AgCl reference electrode and a Pt wire counter electrode (1× PBS, pH 7.2). Responses are provided for a needle having a single coating, two coatings, or three coatings of the insulator. As can be seen, three coatings of the ceramic resin provided a passivated needle, such that the needle itself is not responsive to spikes of $H_2O_2$.

Figure 10A:
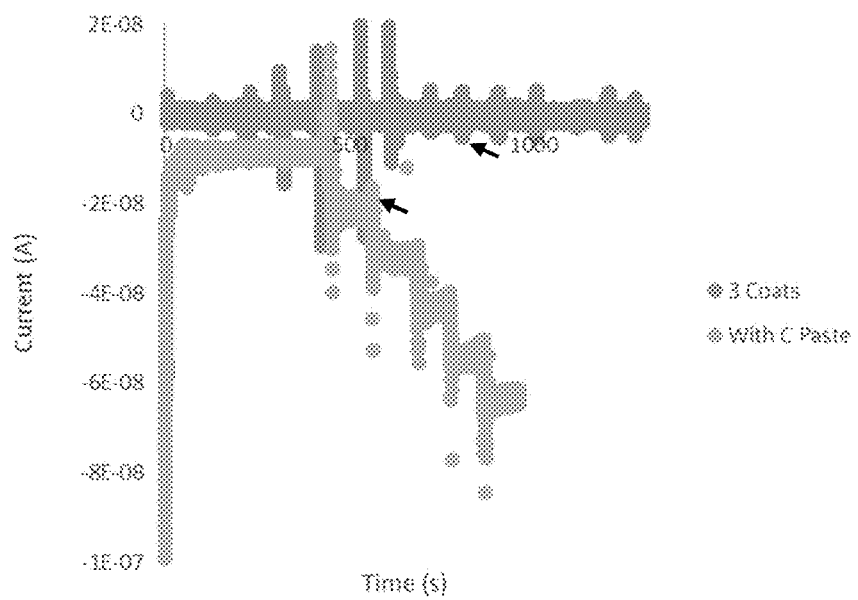
FIG. 10A-10B shows use of an exemplary conductive component packed as a sensor within an insulated needle. Provided are the response of an insulated, packed needle to H$_2$O$_2$ (FIG. 10A, arrow indicates spike of 133 µM H$_2$O$_2$) and an image of the needle (FIG. 10B).
Figure 10B:
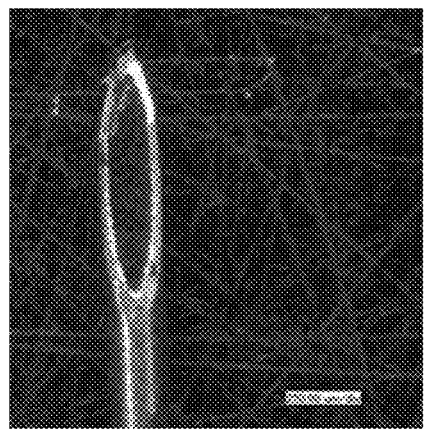

A conductive component was deposited within the needle to ensure that the passivated needle has minimal response to $H_2O_2$, but that an electrochemical response was detected when a carbon paste was provided within the passivated needle and in electrical contact with the transducing wire within the passivated needle. The carbon paste provides a conductive component that is responsive to the presence of $H_2O_2$. FIG. 10A shows the response of an insulated needle (three coats of a ceramic resin) and of an insulated needle packed with carbon paste at its tip. As can be seen, the insulated needle showed minimal response to the $H_2O_2$ test solution. FIG. 10B shows a photograph of a needle insulated with the ceramic resin, in which an electrical connection to the paste is formed with a transducing wire disposed within the needle. If an enzyme such as LOx is added to the carbon paste, then an enzymatic lactate biosensor can be fabricated.

Additional characterization studies were performed to determine the surface chemistry of the needle. In particular, we studied the hydrophobicity of the inner lumen, and the effect of surface chemistry and surface treatment on hydrophobicity measurements (e.g., as determined by contact angle). Surface chemistry and treatment included UV-ozone cleaned needles, insulated needles (with a ceramic resin, such as Ceramix or Kliar coatings from Legor Group), or silanized needles (with a PEG silane).

Figure 11:
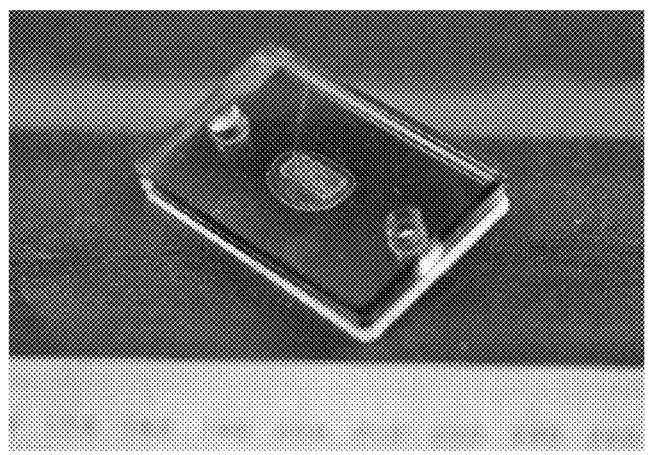
FIG. 11 shows an exemplary prototype device including an array of needles.

An array of needles and transducing wire can be provided within a sensor device in any useful manner. FIG. 11 provides an exemplary disposable sensor device (30 mm by 50 mm), which includes needles incorporated with laminate chip technology. This prototype device was designed to connect the on-chip sensors to a bench-top potentiostat, which can measure and record data from the on-chip sensors. In one non-limiting embodiment, the array includes four needles: a working electrode (e.g., that can function as a lactate biosensor); a reference electrode (e.g., a Pt coaxial transducing wire or a Ag-coated pen needle); an auxiliary electrode (e.g., a bare pen needle); and a reference biosensor (e.g., that has the same specifications as the working electrode but lacks an enzyme, which provides a signal that can be employed to compensate for noise fluctuations).

Other Embodiments

All publications, patents, and patent applications mentioned in this specification are incorporated herein by reference to the same extent as if each independent publication or patent application was specifically and individually indicated to be incorporated by reference.

While the invention has been described in connection with specific embodiments thereof, it will be understood that it is capable of further modifications and this application is intended to cover any variations, uses, or adaptations of the invention following, in general, the principles of the invention and including such departures from the present disclosure that come within known or customary practice within the art to which the invention pertains and may be applied to the essential features hereinbefore set forth, and follows in the scope of the claims.

Other embodiments are within the claims.

The invention claimed is:

1. A device comprising:
   a hollow needle, wherein the needle has an interior surface facing a hollow lumen and an exterior surface, a distal end of the exterior surface comprises a puncturing edge, and the needle has a length of less than about 1.5 mm and/or a width or diameter of less than about 1 mm in order to avoid capillary beds in a tissue and measure a dermal interstitial fluid,
   at least one transducing wire disposed within the lumen of the needle, each transducing wire comprising a surface within the lumen and a distal end comprising an exposed surface and wherein the exposed surface of each transducing wire is conductive and optionally comprises one or more electrochemical modifications; and an insulating layer disposed upon and completely covering the surface of each transducing wire within the lumen whilst leaving the conducting surface at the distal end directly in tissue contact and exposed to the dermal interstitial fluid.

2. The device of claim 1, wherein the puncturing edge of the needle comprises a needle face, wherein the exposed surface comprises a wire face with the conductive surface disposed at a distal end.

3. The device of claim 1, further comprising a conductive component providing an electrical connection to the transducing wire.

4. The device of claim 3, wherein the conductive component comprises a carbon-based paste or a conductive polymer.

5. The device of claim 1, further comprising a conductive component disposed on the exposed surface of the transducing wire, wherein the conductive component optionally comprises one or more entrapped capture agents.

6. The device of claim 1, wherein the at least one transducing wire comprises a first transducing wire and a second transducing wire, wherein the first transducing wire provides a working electrode and the second transducing wire provides a counter electrode or a reference electrode.

7. The device of claim 1, wherein a surface of the hollow needle is coated with a metal reference material.

8. The device of claim 7, wherein the metal reference material comprises a noble metal.

9. The device of claim 8, wherein the noble metal comprises silver, gold, or platinum.

* * * * *